United States Patent
Fuchiwaki et al.

(10) Patent No.: US 12,268,088 B2
(45) Date of Patent: Apr. 1, 2025

(54) LIGHT EMISSION MATERIAL AND ORGANIC ELECTROLUMINESCENCE DEVICE INCLUDING THE SAME

(71) Applicant: Samsung Display Co., Ltd., Yongin-Si (KR)

(72) Inventors: Junta Fuchiwaki, Yokohama (JP); Tohru Sato, Kyoto-si (JP)

(73) Assignee: Samsung Display Co., Ltd., Yongin-si (KR)

( * ) Notice: Subject to any disclaimer, the term of this patent is extended or adjusted under 35 U.S.C. 154(b) by 408 days.

(21) Appl. No.: 15/855,898

(22) Filed: Dec. 27, 2017

(65) Prior Publication Data
US 2018/0294419 A1    Oct. 11, 2018

(30) Foreign Application Priority Data

Apr. 6, 2017 (KR) .................. 10-2017-0044684

(51) Int. Cl.
*H10K 85/60* (2023.01)
*C07D 209/86* (2006.01)
(Continued)

(52) U.S. Cl.
CPC ....... H10K 85/6572 (2023.02); C07D 209/86 (2013.01); C07D 209/88 (2013.01);
(Continued)

(58) Field of Classification Search
CPC ............ H01L 51/0072; H01L 51/5012; C07D 209/82; C07D 209/86; C09K 2211/1007; C09K 11/06; H01K 85/6572; H01K 85/60
See application file for complete search history.

(56) References Cited

U.S. PATENT DOCUMENTS 6,670,054 B1 * 12/2003 Hu .................. C07D 209/86
                                                                252/301.16
6,803,126 B2   10/2004 Sotoyama et al.
(Continued)

FOREIGN PATENT DOCUMENTS

CN    1488707 A  *  4/2004
CN    101481611 A  *  7/2009
(Continued)

OTHER PUBLICATIONS

Sigalov, Mark. "Novel Fluorescent Stilbene Analogs Involving a Carbazole Moiety." Tetrahedron Letters.41 (2000): 8573-8576.) (Year: 2000).*

(Continued)

*Primary Examiner* — Jenna N Chandhok
(74) *Attorney, Agent, or Firm* — Womble Bond Dickinson (US) LLP

(57) ABSTRACT

A light emission material includes a first compound satisfying Equation 1:

$$K2 \geq 0.1 K1. \qquad \text{Equation 1}$$

In Equation 1, K1 is a sum of radiationless transition rate due to internal conversion from a certain specific n-th triplet excitation state to a lower order triplet excitation state including the lowest triplet excitation state, K2 is a reverse intersystem crossing transition rate from the certain specific n-th triplet excitation state to a singlet excitation state which is adjacent to the n-th triplet excitation state, and n is an integer of 2 or more. An organic electroluminescence device including the light emission material may simultaneously attain high emission efficiency and roll-off reduction.

17 Claims, 3 Drawing Sheets

(51) Int. Cl.

| | | |
|---|---|---|
| *C07D 209/88* | (2006.01) | |
| *C07D 221/08* | (2006.01) | |
| *C07F 7/08* | (2006.01) | |
| *C09K 11/02* | (2006.01) | |
| *C09K 11/06* | (2006.01) | |
| *H10K 50/11* | (2023.01) | |
| *H10K 50/12* | (2023.01) | |
| *H10K 50/15* | (2023.01) | |
| *H10K 50/16* | (2023.01) | |
| *H10K 50/17* | (2023.01) | |
| *H10K 50/81* | (2023.01) | |
| *H10K 50/82* | (2023.01) | |
| *H10K 85/40* | (2023.01) | |
| *H10K 101/30* | (2023.01) | |
| *H10K 101/40* | (2023.01) | |

(52) U.S. Cl.
CPC .......... *C07D 221/08* (2013.01); *C07F 7/0814* (2013.01); *C07F 7/0816* (2013.01); *C09K 11/025* (2013.01); *C09K 11/06* (2013.01); *H10K 50/11* (2023.02); *H10K 85/40* (2023.02); *H10K 85/60* (2023.02); *H10K 85/622* (2023.02); *C09K 2211/1007* (2013.01); *C09K 2211/1014* (2013.01); *H10K 50/121* (2023.02); *H10K 50/15* (2023.02); *H10K 50/16* (2023.02); *H10K 50/17* (2023.02); *H10K 50/171* (2023.02); *H10K 50/81* (2023.02); *H10K 50/82* (2023.02); *H10K 2101/30* (2023.02); *H10K 2101/40* (2023.02)

(56) References Cited

U.S. PATENT DOCUMENTS

| | | | |
|---|---|---|---|
| 7,034,454 B2 | 4/2006 | Kawai et al. | |
| 8,957,236 B2 | 2/2015 | Zhang et al. | |
| 2004/0115476 A1* | 6/2004 | Oshiyama | C09K 11/06 313/506 |
| 2006/0247140 A1* | 11/2006 | Cressey | C10M 133/12 508/551 |
| 2006/0284140 A1* | 12/2006 | Breuning | C09B 23/145 252/301.35 |
| 2009/0323747 A1* | 12/2009 | Nakanotani | H01S 5/36 372/43.01 |
| 2014/0135530 A1* | 5/2014 | Zhang | H01L 51/005 568/15 |
| 2016/0190478 A1 | 6/2016 | Nakanotani et al. | |
| 2018/0047910 A1* | 2/2018 | Low | H01L 51/0059 |
| 2021/0408379 A1 | 12/2021 | Numata et al. | |

FOREIGN PATENT DOCUMENTS

| | | | | |
|---|---|---|---|---|
| EP | 1424381 A2 * | 6/2004 | | C09K 11/06 |
| JP | 2003-272864 A | 9/2003 | | |
| JP | 2004-214180 A | 7/2004 | | |
| JP | 2008-098433 A | 4/2008 | | |
| JP | 4378225 B2 | 12/2009 | | |
| JP | 2013-6788 A | 1/2013 | | |
| JP | 2015-179809 A | 10/2015 | | |
| KR | 20090014458 A * | 2/2009 | | |
| KR | 20120052499 A * | 5/2012 | | |
| KR | 1020170025990 A | 3/2017 | | |
| WO | WO-0220694 A1 * | 3/2002 | | C07D 209/86 |
| WO | WO2002020694 A1 * | 3/2002 | | |
| WO | WO-2011136482 A1 * | 11/2011 | | C07C 211/50 |
| WO | WO 2012/176864 A1 | 12/2012 | | |
| WO | WO-2016141693 A1 * | 9/2016 | | C07D 213/16 |

OTHER PUBLICATIONS

Machine Translation of JP2008098433 (Year: 2008).*
Machine Translation of CN101481611 (Year: 2009).*
Xu, Jian et al. Syntheses and Electroluminescnece of Carbazole Substituted Distyrylarylene. Chinese Journal of Chemistry. 23 (2005): 454-458 (Year: 2005).*
Shi, Heping et al. "Synthesis, Aggregation-Induced Emission, and Electroluminescence Properties of a Novel Emitter Comprising Tetraphenylethene and Carbazole Moieties." Synthetic Metals 220 (2016): 356-361. (Year: 2016).*
Machine Translation of KR20120052499 (Year: 2012).*
Machine Translation of KR20090014458 (Year: 2009).*
Machine Translation of CN1488707 (Year: 2004).*
Hu, et al., "Bisanthracene-Based Donor-Acceptor-type Light-Emitting Dopants: Highly Efficient Deep-Blue Emission in Organic Light-Emitting Devices," Advanced Functional Materials, 24, pp. 2064-2071 (2014).
Wu, et al., "Highly efficient blue organic light-emitting diode with high color purity using 4,4'-N,N'-dicarbazole-biphyenyl (CBP) doped with 1,4-bis[2-(3-N-ethylcarbazoryl)vinyl]benzene (BCzVB)," Journal of the Society for Information Display, Dec. 4, 2004, pp. 501-504.
Yao, et al., "Highly Efficient Near-Infrared Organic Light-Emitting Diode Based on a Butterfly-Shaped Donor-Acceptor Chromophore with Strong Solid-State Fluorescence and a Large Proportion of Radiative Excitons," Angew. Chem. vol. 53, Issue 8, Feb. 17, 2014, pp. 2119-2123.
Uoyama, et al., "Highly efficient organic light-emitting diodes from delayed fluorescence," Nature, vol. 492, Dec. 13, 2012, pp. 234-240.
Uejima, et al., "Quantum yield in blue-emitting anthracene derivatives: vibronic coupling density and transition dipole moment density," Phys. Chem. Chem. Phys. 16, 14244-14256, (2014).
Yokoyama, Daisuke et al., "Horizontal orientation of linear-shaped organic molecules having bulky substituents in neat and doped vacuum-deposited amorphous films", Organic Electronics 10 (2009) 127-137 (11 pages).

* cited by examiner

LIGHT EMISSION MATERIAL AND ORGANIC ELECTROLUMINESCENCE DEVICE INCLUDING THE SAME

CROSS-REFERENCE TO RELATED APPLICATION

This application claims priority to and the benefit of Korean Patent Application No. 10-2017-0044684, filed on Apr. 6, 2017, the entire content of which is hereby incorporated by reference.

BACKGROUND

One or more embodiments of the present disclosure herein relate to a light emission material with high efficiency and an organic electroluminescence device including the same.

The development of an organic electroluminescence display as an image display device using an organic electroluminescence device is being actively conducted. Unlike a liquid crystal display, the organic electroluminescence display is a self-luminescent display, in which holes and electrons injected from a first electrode and a second electrode recombine in an emission layer, and a light emission material, which is an organic compound included in the emission layer, emits light to attain display.

An example organic electroluminescence device includes, for example, a first electrode, a hole transport layer disposed (e.g., positioned) on the first electrode, an emission layer disposed on the hole transport layer, an electron transport layer disposed on the emission layer, and a second electrode disposed on the electron transport layer. Holes are injected from the first electrode, and the injected holes move via the hole transport layer and are injected to the emission layer. Meanwhile, electrons are injected from the second electrode, and the injected electrons move via the electron transport layer and are injected to the emission layer. The holes and electrons injected to the emission layer recombine in the emission layer to produce excitons. The organic electroluminescence device emits light using light generated during the transition of the excitons to a ground state. However, the organic electroluminescence device is not limited to the above-described configuration, but various modifications may be possible.

Organic electroluminescence device may be a fluorescent organic electroluminescence device or a phosphorescent organic electroluminescence device, depending on the principle of light emission. The fluorescent organic electroluminescence device has a limitation in that external quantum efficiency is difficult to attain over about 5%, and the phosphorescent organic electroluminescence device has a limitation of weak driving durability. In order to improve the limitations of a common fluorescent organic electroluminescence device and phosphorescent organic electroluminescence device, a fluorescent organic electroluminescence device using a phenomenon of producing singlet excitons by the collision of triplet excitons (triplet-triplet annihilation, TTA), a fluorescent organic electroluminescence device using a thermally activated delayed fluorescence (TADF), etc. are suggested.

SUMMARY

One or more aspects of one or more embodiments of the present disclosure are directed toward a light emission material having high efficiency.

One or more aspects of one or more embodiments of the present disclosure are directed toward an organic electroluminescence device which is capable of attaining high efficiency and roll-off reduction at the same time.

An embodiment of the present disclosure provides a light emission material including a first compound satisfying the following Equation 1.

$$K2 \geq 0.1 K1 \qquad \text{Equation 1}$$

In Equation 1, K1 is a sum of radiationless transition rate due to internal conversion from a certain specific n-th triplet excitation state to a lower order triplet excitation state including the lowest triplet excitation state, and K2 is a reverse intersystem crossing transition rate from the certain specific n-th triplet excitation state to a singlet excitation state which is adjacent to the n-th triplet excitation state, and n is an integer of 2 or more.

In an embodiment, K1 may be about $1 \times 10^9$ $s^{-1}$ or less.

In an embodiment, the first compound may further satisfy the following Equation 2.

$$Vn < 1.5 \times 10^{-4} \text{ (atomic unit)}. \qquad \text{Equation 2}$$

In Equation 2, Vn is defined with respect to a certain specific n-th triplet excitation state and is a maximum value among off-diagonal vibronic coupling constants against each standard vibration mode calculated by quantum chemical calculation between the n-th triplet excitation state and the lowest triplet excitation state.

In an embodiment, the light emission material according to an embodiment of the present disclosure may have a maximum light emission wavelength of about 480 nm or less.

In an embodiment, the first compound may be represented by the following Formula 1:

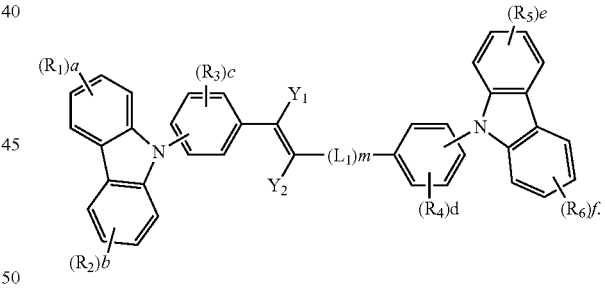

Formula 1

In Formula 1, $L_1$ is a divalent substituted or unsubstituted alkenyl group having 2 to 10 carbon atoms, or a substituted or unsubstituted arylene group having 6 to 30 carbon atoms for forming a ring, m is an integer of 0 to 3, and when m is 2 or more, plurality of $L_1$ are the same or different, $R_1$ to $R_6$ are each independently selected from hydrogen, deuterium, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, and a substituted or unsubstituted heteroaryl group having 2 to 30 carbon atoms for forming a ring, a to f are each independently an integer of 0 to 4, and $Y_1$ and $Y_2$ are each independently selected from hydrogen, deuterium, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring.

In an embodiment, the first compound may be represented by the following Formula 2:

Formula 2

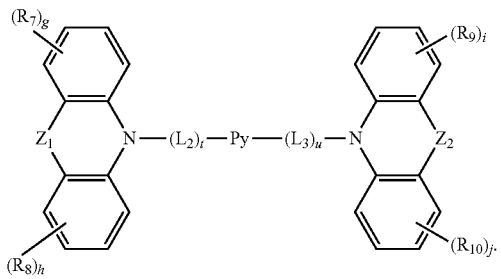

In Formula 2, $L_2$ and $L_3$ are each independently a substituted or unsubstituted arylene group having 6 to 30 carbon atoms for forming a ring, t and u are each independently 0 or 1, $Z_1$ and $Z_2$ are each independently a direct linkage, $CR_{11}R_{12}$, or $SiR_{13}R_{14}$, $R_7$ to $R_{14}$ are each independently selected from hydrogen, deuterium, a halogen atom, a substituted or unsubstituted alkyl group having 1 to 20 carbon atoms, a substituted or unsubstituted aryl group having 6 to 30 carbon atoms for forming a ring, and a substituted or unsubstituted heteroaryl group having 2 to 30 carbon atoms for forming a ring, and one or more $R_7$ to $R_{14}$ are optionally combined with an adjacent group selected from $R_7$ to $R_{14}$ to form a ring, g to j are each independently an integer of 0 to 4, and Py is represented by the following Formula 3:

Formula 3

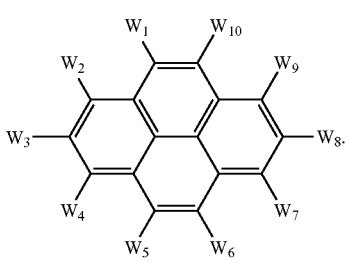

In Formula 3, two of $W_1$ to $W_{10}$ are connecting parts, and the remaining $W_1$ to $W_{10}$ are each independently selected from hydrogen, deuterium, a substituted or unsubstituted alkyl group having 1 to 20 carbon atoms, a substituted or unsubstituted aryl group having 6 to 30 carbon atoms for forming a ring, and a substituted or unsubstituted heteroaryl group having 2 to 30 carbon atoms for forming a ring.

In an embodiment, the light emission material according to an embodiment of the present disclosure may further include a second compound, and the lowest triplet excitation energy level of the second compound may be higher than the lowest singlet excitation energy level of the first compound.

In an embodiment, the second compound may be represented by one of the following Formulae 4 to 6:

Formula 4

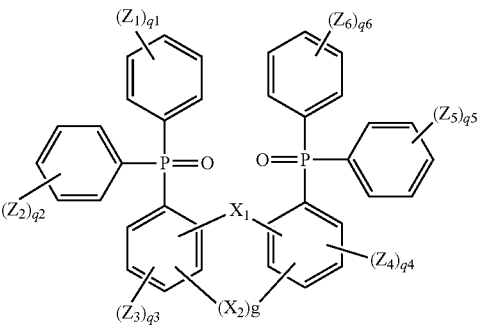

Formula 5

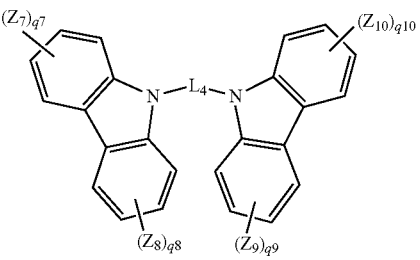

Formula 6

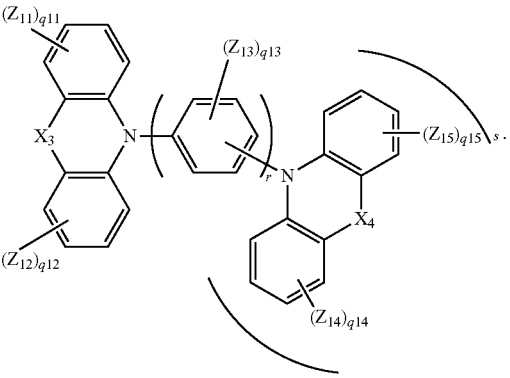

In Formulae 4 to 6, $X_1$ to $X_4$ are each independently O, S, CRaRb, or SiRcRd, Ra to Rd and $Z_1$ to $Z_{15}$ are each independently selected from hydrogen, deuterium, a halogen atom, a substituted or unsubstituted alkyl group having 1 to 20 carbon atoms, a substituted or unsubstituted aryl group having 6 to 30 carbon atoms for forming a ring, and a substituted or unsubstituted heteroaryl group having 2 to 30 carbon atoms for forming a ring, g and s are each independently 0 or 1, $q_1$, $q_2$, $q_5$, $q_6$ and $q_{13}$ are each independently an integer of 0 to 5, $q_3$, $q_4$, $q_7$ to $q_{12}$, $q_{14}$ and $q_{15}$ are each independently an integer of 0 to 4, $L_4$ is a substituted or unsubstituted arylene group having 6 to 30 carbon atoms for forming a ring, or a substituted or unsubstituted heteroarylene group having 2 to 30 carbon atoms for forming a ring, and r is 1 or 2.

In an embodiment, the light emission material according to an embodiment of the present disclosure may have a light emission mechanism based on transition from a singlet state to a ground state.

In an embodiment of the present disclosure, an organic electroluminescence device includes a first electrode, a hole transport region on the first electrode, an emission layer on the hole transport region, an electron transport region on the emission layer, and a second electrode on the electron transport region, wherein the emission layer includes the light emission material according to an embodiment of the present disclosure.

In an embodiment, the emission layer may include a host and a dopant, and the dopant may be a first compound and the host may be a second compound.

In an embodiment, the lowest triplet excitation energy level of the host may be higher than the lowest singlet excitation energy level of the dopant.

In an embodiment, the emission layer may be a fluorescence emission layer, and a maximum external quantum yield of the organic electroluminescence device may be about 5% or more.

BRIEF DESCRIPTION OF THE FIGURES

The accompanying drawings are included to provide a further understanding of the present disclosure, and are incorporated in and constitute a part of this specification. The drawings illustrate example embodiments of the present disclosure and, together with the description, serve to explain principles of the present disclosure.

In the drawings:

FIG. 3 illustrates a relation between the lowest singlet energy level of a first compound and the lowest triplet energy level of a second compound, which are included in the light emission material according to an embodiment of the present disclosure;

DETAILED DESCRIPTION

Figure 1:
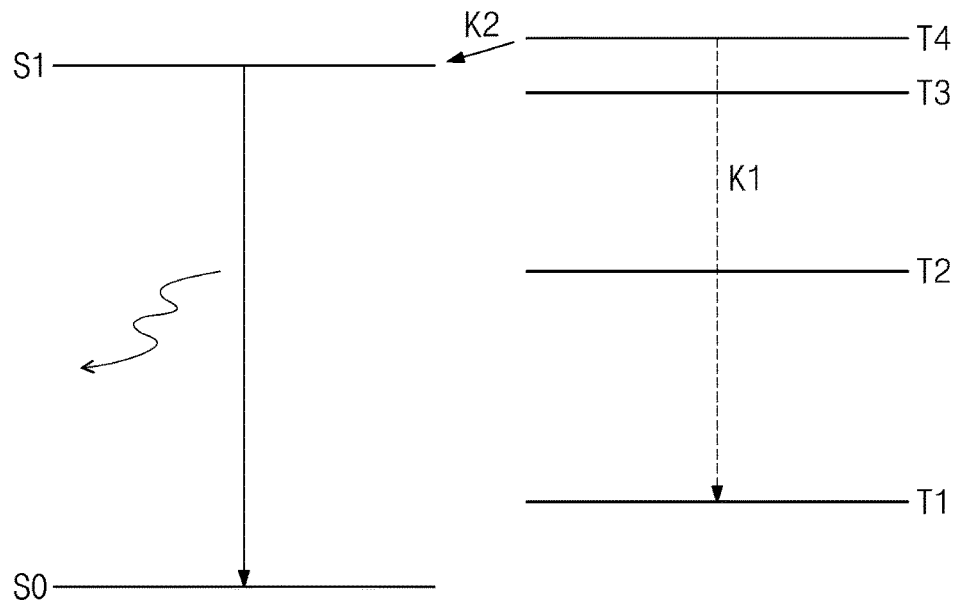
FIG. 1 is an energy diagram of an excited state of a first compound, which is included in a light emission material according to an embodiment of the present disclosure.

The above objects, other objects, features and advantages of the present disclosure will be easily understood from example embodiments with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art.

Like reference numerals refer to like elements throughout. In the drawings, the dimensions of structures may be exaggerated for clarity of illustration. It will be understood that, although the terms "first," "second," etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof. It will also be understood that when a layer, a film, a region, a plate, etc. is referred to as being "on" another part, it can be directly on the other part, or intervening layers may also be present. In contrast, it will be understood that when a layer, a film, a region, a plate, etc. is referred to as being 'under' another part, it can be directly under, or intervening layers may also be present.

First, referring to FIGS. 1 to 3, a light emission material according to an embodiment of the present disclosure will be explained.

The light emission material according to an embodiment of the present disclosure includes a first compound satisfying the following Equation 1:

$$K2 \geq 0.1 K1. \qquad \text{Equation 1}$$

In Formula 1, K1 is a sum of radiationless transition rate due to internal conversion from a certain specific n-th triplet excitation state to a lower order triplet excitation state including the lowest triplet excitation state, K2 is a reverse intersystem crossing transition rate from a certain specific n-th triplet excitation state to a singlet excitation state adjacent to the n-th triplet excitation state, and n (in the n-th triplet excitation state) is an integer greater than 2.

For example, the first compound is a compound having a radiationless inactivation rate from an n-th triplet excitation state to the lowest triplet excitation state greater by about 0.1 times than a reverse intersystem crossing rate of transition from an n-th triplet excitation state to a singlet excitation state adjacent to the n-th triplet excitation state. If K2 is greater than K1, but not greater by 0.1 times or more, the resulting effects due to the fact that K2 is greater than K1 might be insignificant. Accordingly, K2 should be greater than K1 by 0.1 times or more, the greater the multiplicity, the better the effect. For example, improved results may be achieved when K2 is greater than K1 by 0.2 times, when compared with a case in which K2 is greater than K1 by 0.1 times.

For example, in the first compound, K2 may be greater than K1 by 0.1 times to 20 times.

In the description, the term "reverse intersystem crossing" may refer to transition from a triplet state to a singlet state.

FIG. 1 is an energy diagram of an excited state of a first compound, which is included in a light emission material according to an embodiment of the present disclosure. In FIG. 1, a case where n (the n-th triplet excitation state) is 4 in Equation 1 is illustrated.

Referring to FIG. 1, in the first compound, since a transition rate K1 (from a fourth triplet excitation state T4 to the lowest triplet excitation state T1) is greater than a transition rate K2 (from a fourth triplet excitation state T4 to a singlet excitation state S1 which is adjacent to the fourth triplet excitation state T4) by about 0.1 times or more, the transition probability of excitons from the fourth triplet excitation state T4 to the adjacent singlet excitation state S1 becomes higher than the transition probability of excitons from the fourth triplet excitation state T4 to triplet excitation states T3, T2 and/or T1, which all have lower energy level than the fourth triplet excitation state T4. Thus, the first compound may emit light via the transition of triplet excitons into singlet excitons and then, the transition of the singlet excitons to a ground state.

The mechanism of emitting light after the transition of triplet excitons to singlet excitons is referred to as a thermally activated delayed fluorescence. The thermally activated delayed fluorescence has higher theoretical efficiency limitation than common fluorescence emission, but a larger amount of heat may be required for the transition from the triplet to the singlet state, and there is a relatively high probability of generating roll-off phenomenon, by which luminance may be dropped drastically under high current density. According to embodiments of the present disclosure, the first compound included in the light emission material uses (utilizes) a triplet excitation state (for example, T3 or T4) having higher energy level than the lowest triplet excitation state T1, and thermal energy required for the transition of the triplet excitons to the singlet excitons is zero or extremely low. As a result, the light emission material according to an embodiment of the present disclosure may attain light emission with high efficiency by including the first compound, and in the case of using the material in an organic electroluminescence device, the possibility of generating the roll-off phenomenon of the organic electroluminescence device may be minimized or reduced.

The light emission material according to an embodiment of the present disclosure is not a thermally activated delayed fluorescence emission material, but is a material for emitting fluorescence via highly excited triplets, which is different from a common fluorescence emission material. For example, a common fluorescence emission material satisfies a relation of K1>K2 and has an IQE value of 0.25 at the most. However, the light emission material according to an embodiment of the present disclosure satisfies a relation of K2>K1 and has an IQE value of 0.32 or more, and may attain IQE=1 like a phosphorescence emission material and a thermally activated delayed fluorescence material. External quantum efficiency is about 20% of IQE, and IQE may be derived by the following equation.

$$IQE = 0.25 + 0.75 \times K2/(K1+K2)$$

In FIG. 1, reverse intersystem crossing, which is transition from a fourth triplet excitation state T4 to the lowest triplet excitation state T1, is illustrated as an embodiment, but an embodiment of the present disclosure is not limited thereto. For example, K2 in Equation 1 may refer to a transition rate from a fifth triplet excitation state (here, n=5 in Equation 1) to a third singlet excitation state. That is, the reverse intersystem crossing target is not specifically limited to n being 2 or more in Equation 1.

In FIG. 1, a transition rate from an n-th triplet excitation state T4 to a singlet excitation state S1, which is adjacent to the n-th triplet excitation state T4 and has a lower energy level, is illustrated as an embodiment of K2 of Equation 1, but an embodiment of the present disclosure is not limited thereto.

Figure 2:
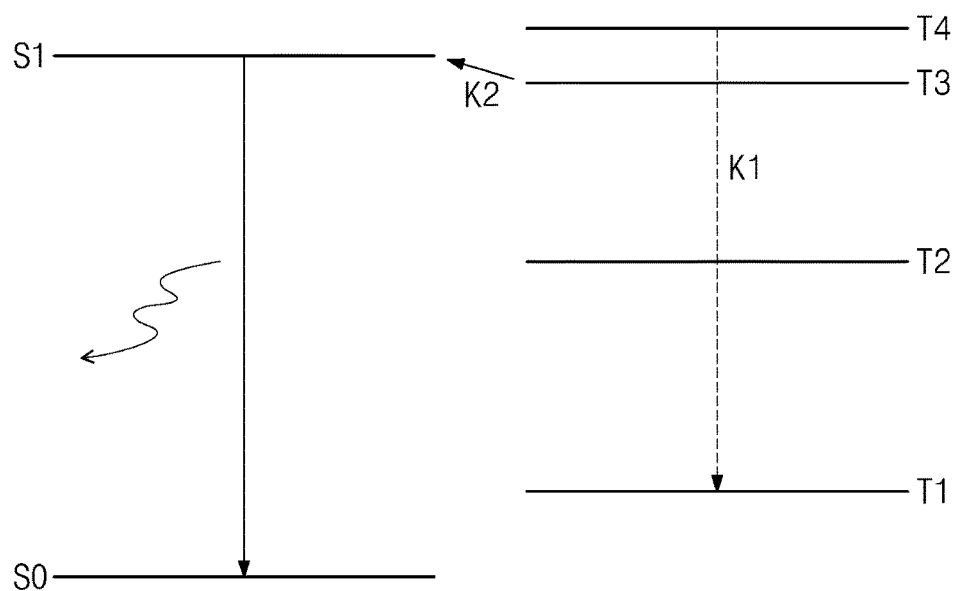
FIG. 2 is an energy diagram of an excited state of a first compound, which is included in a light emission material according to another embodiment of the present disclosure.

Referring to FIG. 2, K2 of Equation 1 may be a transition rate from a third triplet excitation state T3 to a singlet excitation state S1 which is adjacent to the third triplet excitation state T3 and has a higher energy level. In other words, for K2, the singlet excitation state adjacent to the n-th triplet excitation state may have higher or lower energy level than the n-th triplet excitation state. In embodiments where the singlet excitation state adjacent to the n-th triplet excitation state has a higher energy level than the n-th triplet excitation state, smaller energy gaps are more desirable.

In Equation 1, K1 may be about $1 \times 10^9$ s$^{-1}$ or less. For example, K1 may be from about $1 \times 10^{-1}$ s$^{-1}$ to about $1 \times 10^9$ s$^{-1}$. For example, a transition rate from a fourth triplet excitation state T4 to the lowest triplet excitation state T1 may be about $1 \times 10^9$ s$^{-1}$ or less. In the case where K1 in Equation 1 has a small value of about $1 \times 10^9$ s$^{-1}$ or less, the inactivation rate by heat of the triplet excitation state may be slow, thereby increasing the possibility of reverse intersystem crossing from a triplet excitation state to an adjacent singlet excitation state.

In FIGS. 1 and 2, light emission of the light emission material according to an embodiment of the present disclosure by the relaxation of excitons from the lowest singlet excitation state to a ground state is illustrated as an embodiment. However, an embodiment of the present disclosure is not limited thereto. For example, the first compound may be a material emitting light by the relaxation of excitons from a second singlet excitation state to a ground state, so long as the first compound satisfied Equation 1.

In an embodiment, the first compound satisfying Equation 1 further satisfies the following Equation 2:

$$Vn < 1.5 \times 10^{-4} \text{ (atomic unit)}. \qquad \text{Equation 2}$$

In Equation 2, Vn is defined with respect to a certain specific n-th triplet excitation state and is the maximum value among off-diagonal vibronic coupling constants against each standard vibration mode calculated by quantum chemical calculation between an n-th (specific n, where n is an integer) triplet excitation state and the lowest triplet excitation state. The first compound satisfying Equation 2 may accomplish a relation K2>0.1K1 via the decrease of K1, by having a relatively small off-diagonal vibronic coupling constant. As a result, due to the transition from a triplet excitation state to a singlet excitation state and the generation of fluorescence emission, higher quantum efficiency may be obtained than when a commonly known fluorescence emission material is used.

The light emission material according to an embodiment of the present disclosure may emit blue light. The maximum light emission wavelength of the light emission material according to an embodiment of the present disclosure may be about 480 nm or less. For example, the light emission material according to an embodiment of the present disclosure may emit blue light in a wavelength region of about 430 nm to about 480 nm.

The structure of the first compound included in the light emission material according to an embodiment of the present disclosure is not specifically limited so long as the first compound satisfies Equation 1. The first compound may be represented by, for example, the following Formula 1. However, the structure of the first compound is not limited to Formula 1.

Formula 1

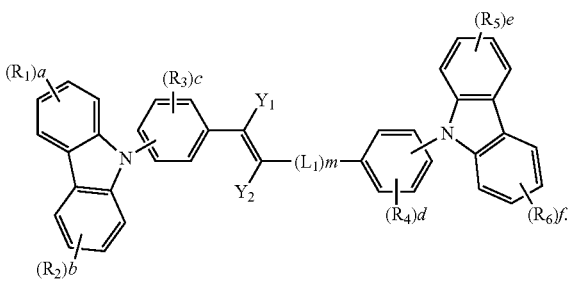

In Formula 1, L$_1$ may be a divalent substituted or unsubstituted alkenyl group, or a substituted or unsubstituted arylene group having 6 to 30 carbon atoms for forming a ring; m is an integer of 0 to 3, and in the case where m is 2 or more, plurality of $L_1$(s) may be the same or different; $R_1$ to $R_6$ may each independently be selected from hydrogen, deuterium, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, and a substituted or unsubstituted heteroaryl group having 2 to 30 carbon atoms for forming a ring; a to f may each independently be an integer of 0 to 4; and $Y_1$ and $Y_2$ may each independently be selected from hydrogen, deuterium, a substituted or unsubstituted alkyl group having 1 to 10 carbon atoms, a substituted or unsubstituted aryl group having 6 to 30 carbon atoms for forming a ring, and a substituted or unsubstituted heteroaryl group having 2 to 30 carbon atoms for forming a ring.

In the present application, the terms "substituted or unsubstituted" may refer to an unsubstituted group or a group substituted with at least one substituent selected from deuterium, a halogen atom, a cyano group, a nitro group, an amino group, a silyl group, a boron group, a phosphine oxide group, a phosphine sulfide group, an alkyl group, an alkenyl group, a fluorenyl group, an aryl group, and a heterocyclic group. In addition, each of the exemplified substituents may be substituted or unsubstituted. For example, a biphenyl group may be designated as an aryl group or as a phenyl group substituted with a phenyl group.

In the present application, the terms "forming a ring via the combination with an adjacent group" may refer to forming a substituted or unsubstituted hydrocarbon cyclic group, or a substituted or unsubstituted heterocyclic group via the combination of one substituent group with an adjacent substituent group. The hydrocarbon cyclic group may include an aliphatic hydrocarbon ring and/or an aromatic hydrocarbon ring. The heterocyclic group may include an aliphatic ring comprising at least one heteroatom and/or an aromatic ring comprising at least one heteroatom. The hydrocarbon cyclic group and the heterocyclic group may each independently be monocyclic or polycyclic. In addition, the ring formed via the combination with an adjacent group may be combined with another ring to form a Spiro structure.

In the present application, the terms "an adjacent group" may refer to a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the present application, the halogen atom may include a fluorine atom, a chlorine atom, a bromine atom and/or an iodine atom.

In the present application, the alkyl group may refer to a linear, branched or cyclic hydrocarbon group. The carbon number of the alkyl group may be from 1 to 30, from 1 to 20, from 1 to 10, or from 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present application, the aryl group may refer to a monocyclic aryl group or a polycyclic aryl group. The carbon number for forming a ring in the aryl group may be 6 to 30, 6 to 20, or 6 to 15. Examples of the aryl group may include phenyl, naphthyl, anthracenyl, phenanthryl, biphenyl, terphenyl, quaterphenyl, quinqphenyl, sexiphenyl, triphenylene, pyrenyl, benzofluoranthenyl, chrysenyl, etc., without limitation.

In the present application, the fluorenyl group may be substituted, and, for example, two substituents may combine to each other to form a spiro structure.

In the present application, the heteroaryl group may refer to a cyclic group including at least one heteroatom selected from O, N, P, Si and S, and carbon atoms as the remaining ring-forming atoms. The carbon number for forming a ring of the heteroaryl group may be 2 to 30, or 2 to 20. The heteroaryl group may include monocyclic heteroaryl group or polycyclic heteroaryl group. The polycyclic heteroaryl group may have dicyclic or tricyclic structure. Examples of the heteroaryl group may include thiophene, furan, pyrrole, imidazole, thiazole, oxazole, oxadiazole, triazole, pyridine, bipyridine, pyrimidine, triazine, triazole, acridine, pyridazine, pyrazine, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, benzothiazole, phenothiazine, dibenzosilole, dibenzofuran, etc., without limitation.

In the present application, explanation on the aryl group may be applied to the arylene group, except that the arylene group is a divalent group.

In the present application, explanation on the heteroaryl group may be applied to the heteroarylene group, except that the heteroarylene group is a divalent group.

In the present application, the silyl group may include alkyl silyl and/or aryl silyl. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc., without limitation.

In the present application, the boron group may include an alkyl boron group and/or an aryl boron group. Examples of the boron group may include a trimethylboron group, a triethylboron group, a t-butyldimethylboron group, a triphenylboron group, a diphenylboron group, a phenylboron group, etc., without limitation.

In the present application, the alkenyl group may be linear or branched hydrocarbon group having at least one carbon-carbon double bond at one or more positions along the hydrocarbon chain of the group. The carbon number is not specifically limited, but may be 2 to 30, 2 to 20, 2 to 10, or 2 to 5. Examples of the alkenyl group may include vinyl, 1-butenyl, 1-pentenyl, 1,3-butadienyl aryl, styrenyl, styrylvinyl, etc., without limitation.

Formula 1 may be represented by the following Formula 1-1. However, an embodiment of the present disclosure is not limited thereto.

Formula 1-1

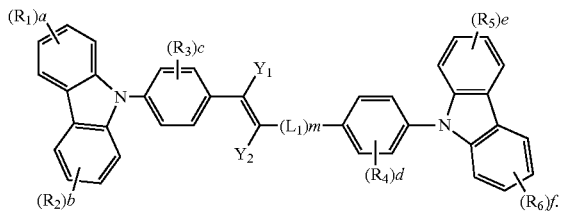

In Formula 1-1, descriptions for $R_1$ to $R_6$, a to f, $Y_1$, $Y_2$ and m may be the same as those provided above.

Formula 1 may be represented by the following Formula 1-2. However, an embodiment of the present disclosure is not limited thereto.

Formula 1-2

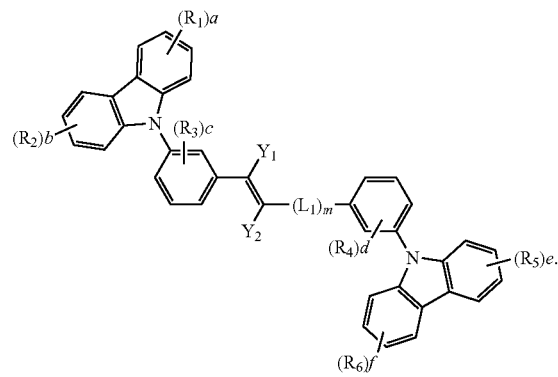

In Formula 1-2, descriptions of $R_1$ to $R_6$, a to f, $Y_1$, $Y_2$ and m may be the same as those provided above.

In Formula 1, m may be 0. In this case, Formula 1 has a structure in which two benzene groups are connected via a divalent ethylene group.

In Formula 1, m may be 1.

In Formula 1, m may be 2, one $L_1$ may be a substituted or unsubstituted arylene group having 6 to 30 carbon atoms for forming a ring, and the remaining one $L_1$ may be a substituted or unsubstituted alkenyl group having 2 to 10 carbon atoms.

In Formula 1, m may be 2, one $L_1$ may be a substituted or unsubstituted phenylene group, and the remaining one $L_1$ may be a substituted or unsubstituted divalent ethylene (vinyl) group.

In Formula 1, m may be 2, one $L_1$ may be a substituted or unsubstituted divalent biphenylene group, and the remaining one $L_1$ may be a substituted or unsubstituted divalent ethylene (vinyl) group.

In Formula 1, m may be 3.

In Formula 1, all $R_1$ to $R_6$ may be hydrogen atoms. However, an embodiment of the present disclosure is not limited thereto, and in Formula 1, at least one of $R_1$ to $R_6$ may be substituted with a substituent other than hydrogen.

In Formula 1, $R_1$ to $R_6$ may be each independently be hydrogen, a fluorine atom, a cyano group, a trimethylsilyl group, a triphenylsilyl group, a substituted or unsubstituted alkyl having 1 to 10 carbon atoms, or a substituted or unsubstituted phenyl group.

In Formula 1, in the case where a is 2 or more, plurality of $R_1$ may be the same or different. In Formula 1, in the case where b is 2 or more, plurality of $R_2$ may be the same or different. In Formula 1, in the case where c is 2 or more, plurality of $R_3$ may be the same or different. In Formula 1, in the case where d is 2 or more, plurality of $R_4$ may be the same or different. In Formula 1, in the case where e is 2 or more, plurality of $R_5$ may be the same or different. In Formula 1, in the case where f is 2 or more, plurality of $R_6$ may be the same or different.

In Formula 1, a, b, e and f may each be 0. However, an embodiment of the present disclosure is not limited thereto, and in Formula 1, at least one of a, b, e and f may be 1 or more. In this case, at least one of $R_1$, $R_2$, $R_5$ and $R_6$ may be a substituted or unsubstituted alkyl group having 1 to 20 carbon atoms, a cyano group, a halogen atom, a trimethylsilyl group or a triphenylsilyl group.

In Formula 1, both c and d may be 0. However, an embodiment of the present disclosure is not limited thereto.

In Formula 1, both $Y_1$ and $Y_2$ may be hydrogen atoms. However, an embodiment of the present disclosure is not limited thereto and, in an embodiment, at least one of $Y_1$ and $Y_2$ may be a substituted or unsubstituted alkyl group having 1 to 10 carbon atoms or a substituted or unsubstituted aryl group having 6 to 30 carbon atoms for forming a ring. In Formula 1, both $Y_1$ and $Y_2$ may be substituted or unsubstituted alkyl groups having 1 to 10 carbon atoms. In Formula 1, both $Y_1$ and $Y_2$ may be substituted or unsubstituted methyl groups. In Formula 1, at least one of $Y_1$ and $Y_2$ may be a substituted or unsubstituted phenyl group.

The first compound may be at least one selected from the compounds represented in the following Compound Group 1. However, an embodiment of the first compound is not limited thereto and the first compound is not specifically limited to the compounds provided below, so long as it satisfies Equation 1 as described above.

Compound Group 1

1-1

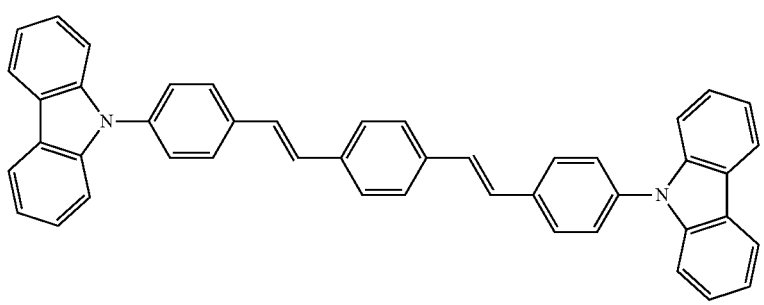

1-2
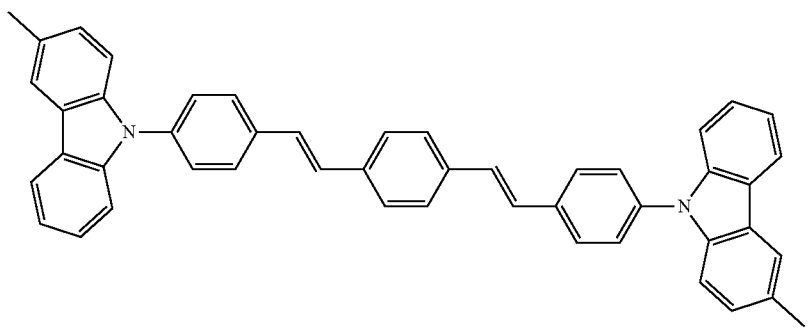
1-3
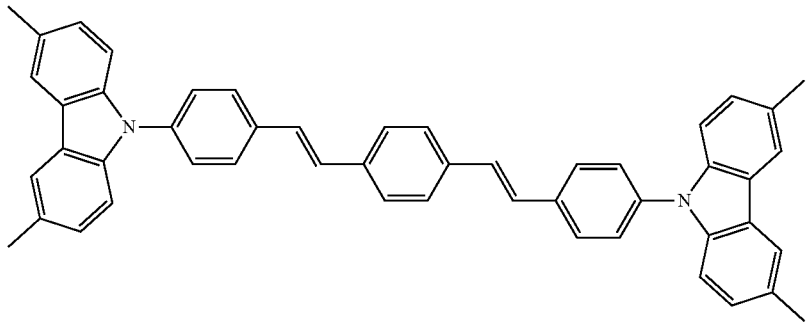
1-4
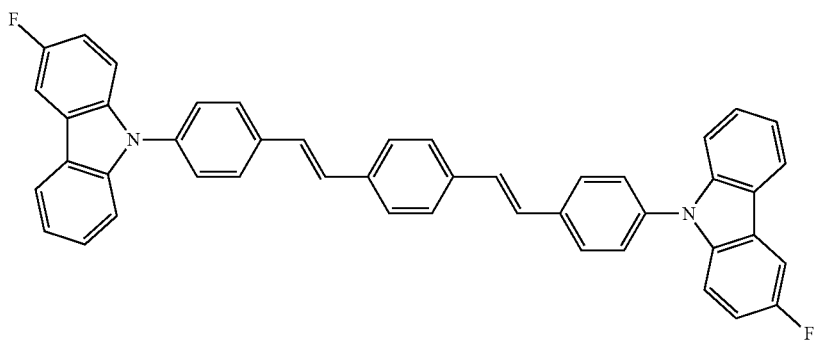
1-5
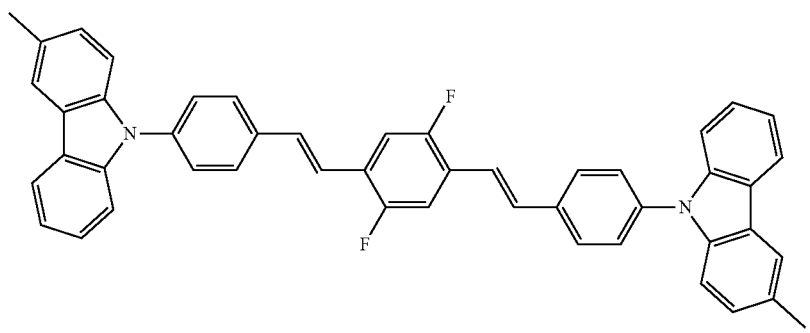

1-6
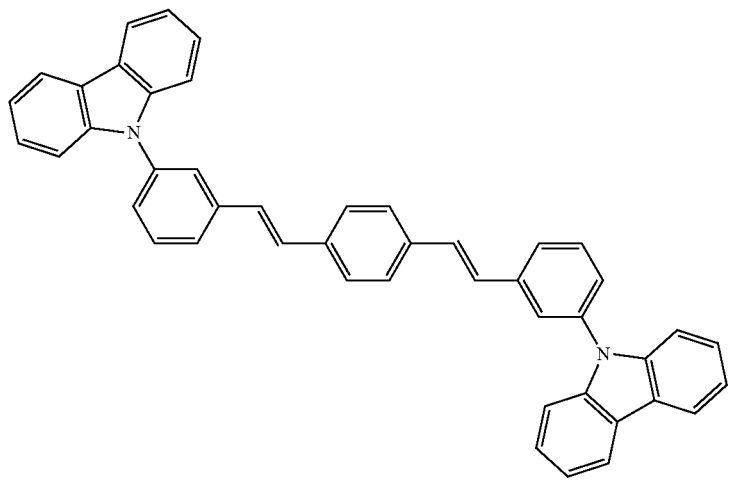
1-7
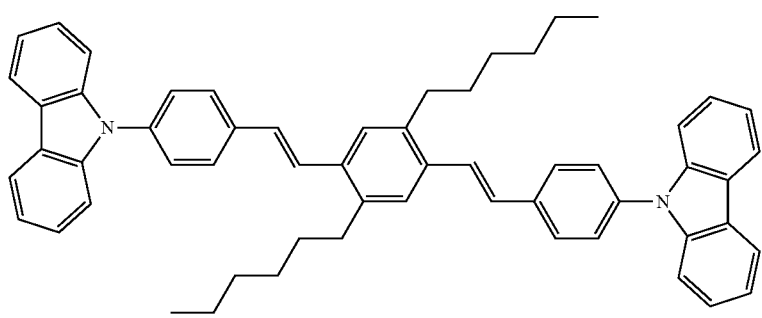
1-8
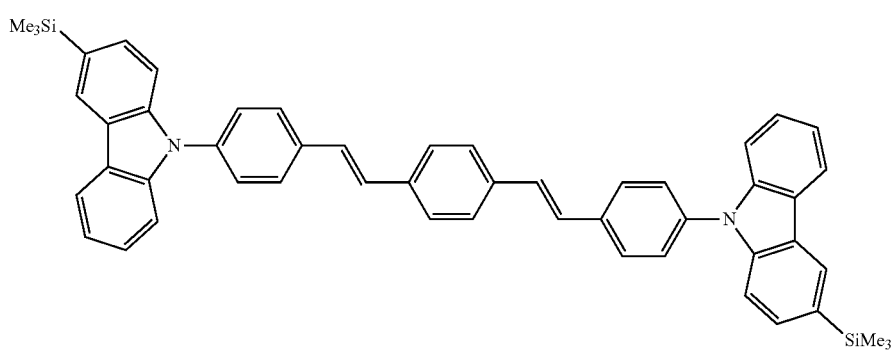
1-9
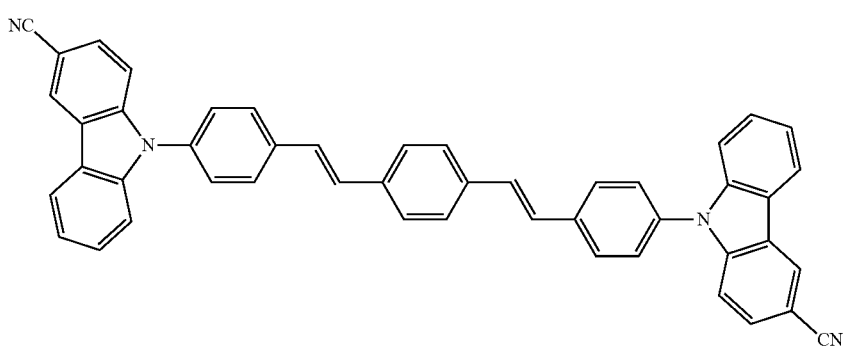

-continued
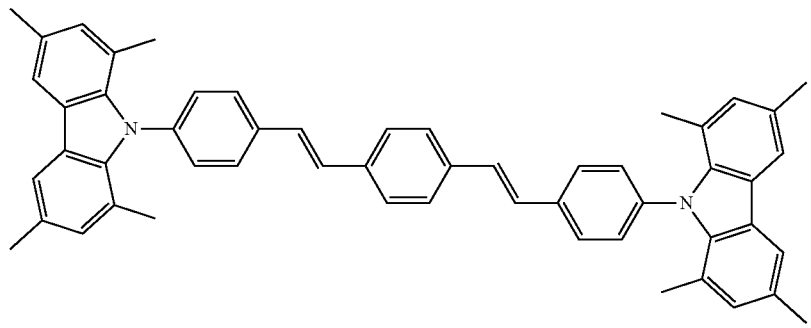
1-10
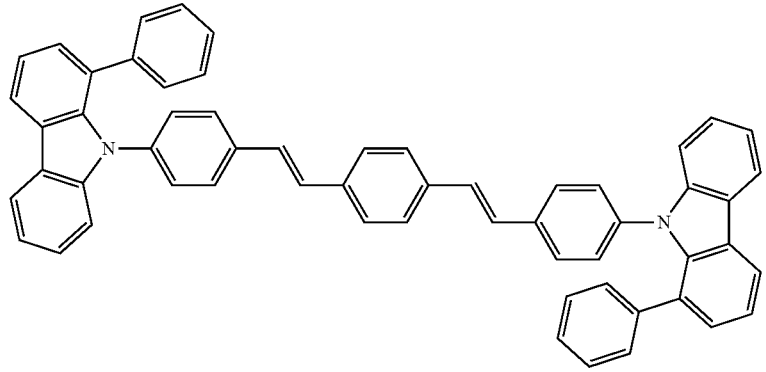
1-11
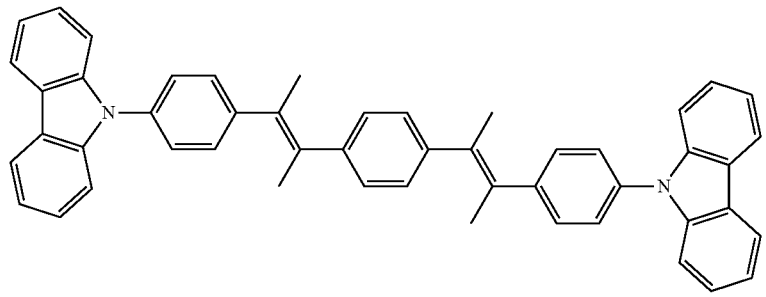
1-12
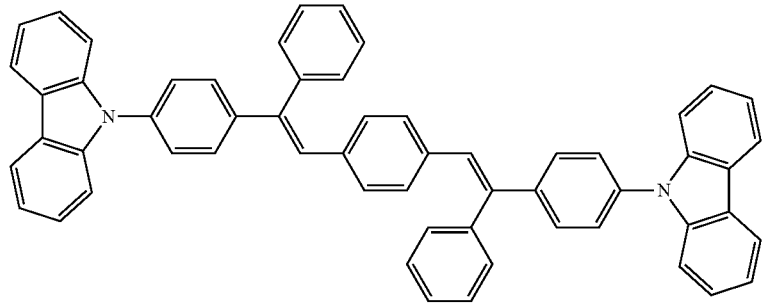
1-13
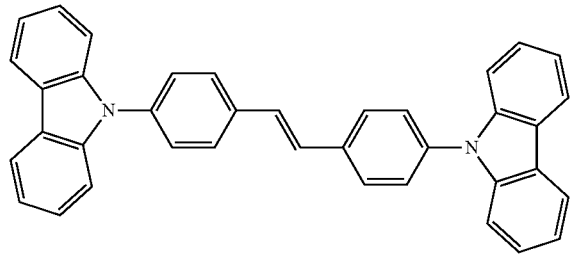
1-14

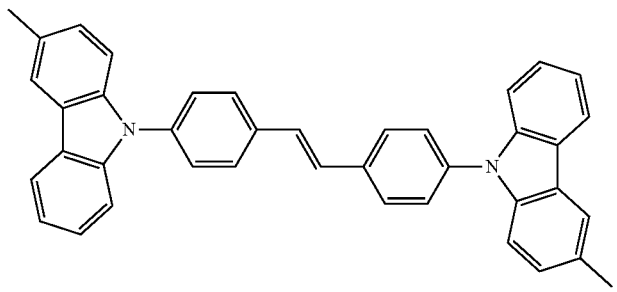
1-15
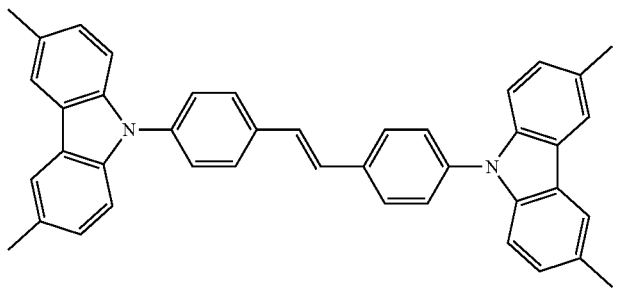
1-16
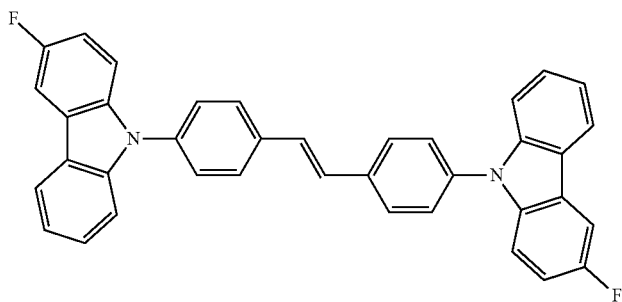
1-17
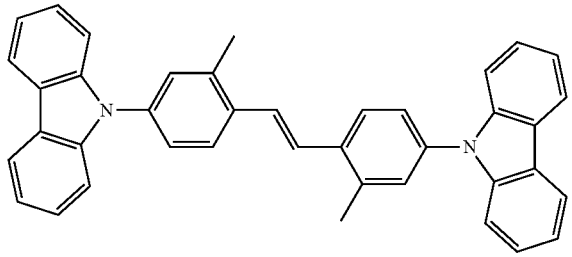
1-18
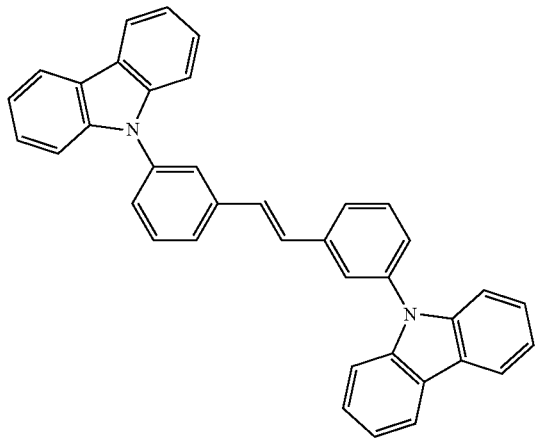
1-19

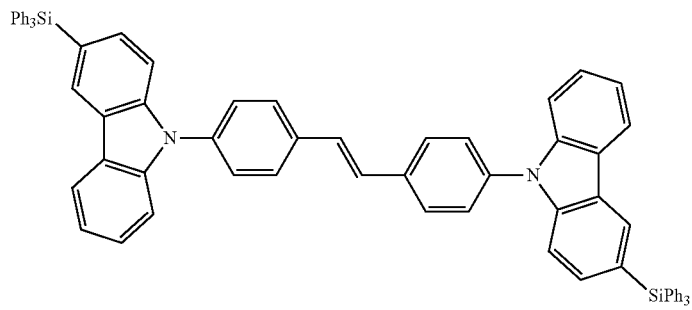
1-20
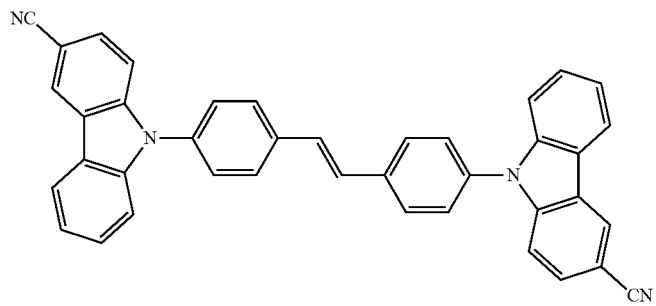
1-21
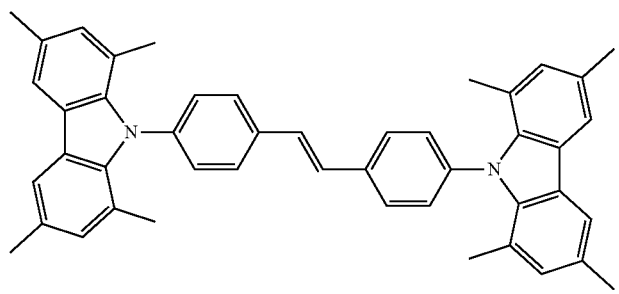
1-22
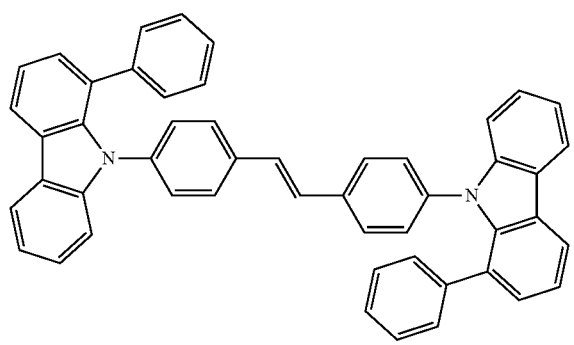
1-23
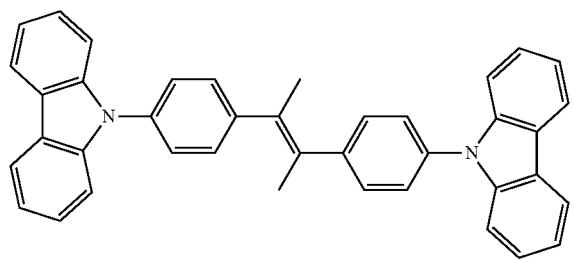
1-24

-continued
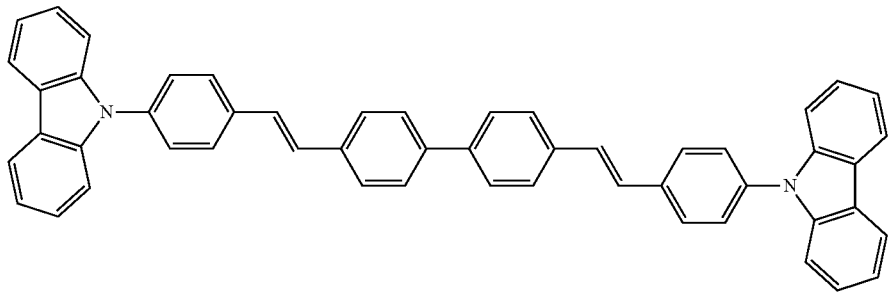
1-25
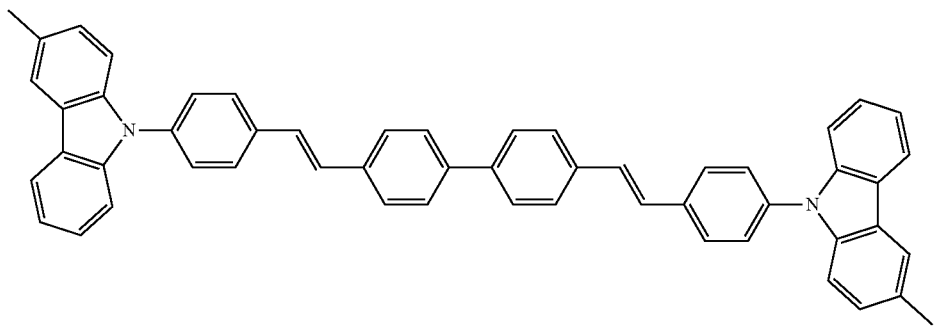
1-26
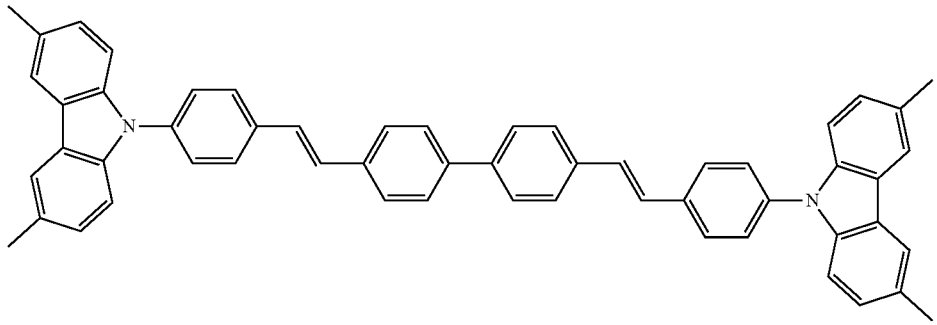
1-27
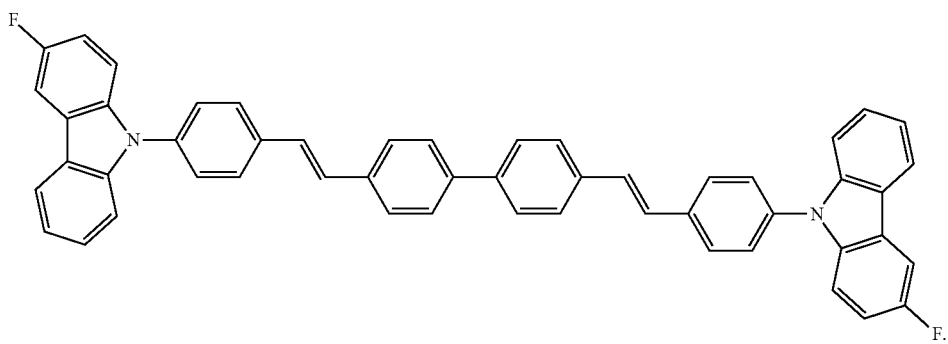
1-28

Another example of the first compound may include the compounds represented by the following Formula 2. However, as discussed above, the structure of the first compound included in the light emission material according to an embodiment of the present disclosure is not specifically limited, so long as the first compound satisfies Equation 1.

Formula 2

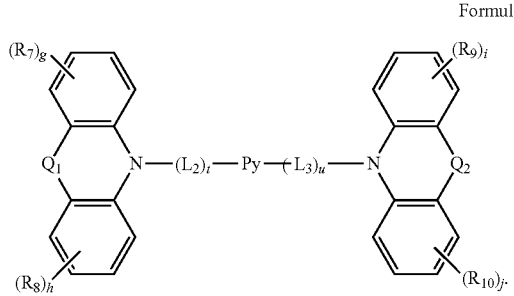

In Formula 2, $L_2$ and $L_3$ may each independently be a substituted or unsubstituted arylene group having 6 to 30 carbon atoms for forming a ring, t and u may each independently be 0 or 1, $Q_1$ and $Q_2$ may each independently be a direct linkage (e.g., a bond such as a single bond), $CR_{11}R_{12}$ or $SiR_{13}R_{14}$, $R_7$ to $R_{14}$ may each independently be hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, and two or more of $R_7$ to $R_{14}$ may be combined with an adjacent group to form a ring, g to j may each independently be an integer of 0 to 4, and Py may be represented by the following Formula 3:

Formula 3

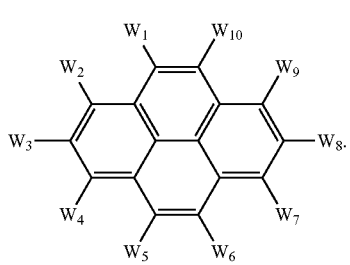

In Formula 3, two among $W_1$ to $W_{10}$ may be connecting parts, and the remaining ones among $W_1$ to $W_{10}$ may each independently be hydrogen, deuterium, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. As used herein, "connecting part" may refer to bonding sites.

In Formula 2, each of $Q_1$ and $Q_2$ may be a direct linkage. When each of $Q_1$ and $Q_2$ is a single bond, for example, compound represented by Formula 2 includes two carbazole groups.

In Formula 2, $L_2$ and $L_3$ may each independently be a substituted or unsubstituted phenylene group. However, an embodiment of the present disclosure is not limited thereto, and each of t and u may be 0.

In Formula 2, $R_{11}$ and $R_{12}$ may be combined with each other to form a ring, and $R_{13}$ and $R_{14}$ may be combined with each other to form a ring.

In Formula 2, each of t and u may be 0, and each of $Q_1$ and $Q_2$ may be $CR_{11}R_{12}$ or $SiR_{13}R_{14}$. Here, $R_{11}$ to $R_{14}$ may each independently be a substituted or unsubstituted aryl group having 6 to 30 carbon atoms for forming a ring, for example, a phenyl group. $R_{11}$ and $R_{12}$ may be combined with each other to form a fluorene ring.

Formula 2 may be represented by the following Formula 2-1. However, an embodiment of the present disclosure is not limited thereto.

Formula 2-1

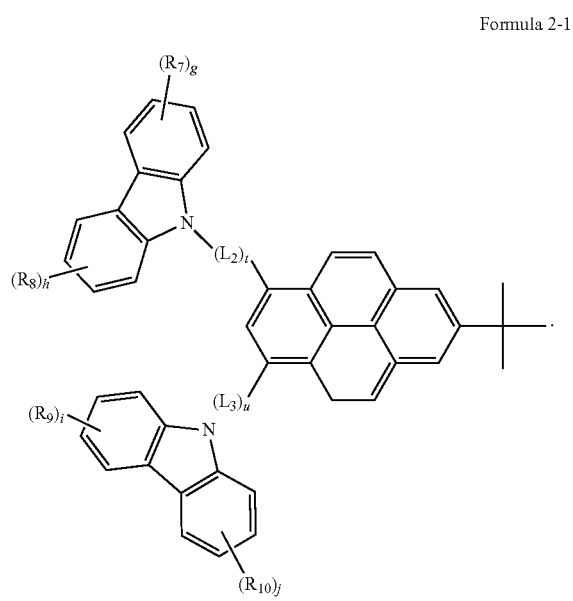

In Formula 2-1, descriptions of $R_7$ to $R_{10}$, g to j, $L_2$, $L_3$, t and u may be the same as those provided above.

In Formula 2-1, each of t and u may be 1, and $L_2$ and $L_3$ may each independently be a substituted or unsubstituted phenylene group. In Formula 2-1, each of t and u may be 1, and $L_2$ and $L_3$ may each be an unsubstituted phenylene group.

In Formula 2-1, each of g to j may be 0. However, an embodiment of the present disclosure is not limited thereto. In some embodiments, an equation of $g+h+i+j \geq 1$ may be satisfied, and at least one of $R_7$ to $R_{10}$ may be a halogen atom or a substituted or unsubstituted alkyl group having 1 to 10 carbon atoms. In Formula 2-1, at least one of $R_7$ to $R_{10}$ may be a fluorine atom or a substituted or unsubstituted methyl group.

In Formula 3, $W_2$ and $W_3$ may be connecting parts (e.g., bonding sites). However, an embodiment of the present disclosure is not limited thereto, and for example, in Formula 3, $W_3$ and $W_8$ may be connecting parts. In another embodiment, $W_4$ and $W_9$ may be connecting parts.

In Formula 2, $Q_1$ and $Q_2$ may be the same, and $L_2$ and $L_3$ may be the same. In Formula 2, $Q_1$ and $Q_2$ may be the same, $L_2$ and $L_3$ may be the same, $R_7$ and $R_9$ may be the same, and $R_8$ and $R_{19}$ may be the same.

In Formula 2, $Q_1$ and $Q_2$ may be $CR_{11}R_{12}$, and $R_{11}$ and $R_{12}$ may each independently be a substituted or unsubstituted aryl group having 6 to 30 carbon atoms for forming a ring, for example, $R_{11}$ and $R_{12}$ may each independently be a substituted or unsubstituted phenyl group. $R_{11}$ and $R_{12}$ may be combined with each other to form a ring, for example, a fluorene ring.

In Formula 2, $Q_1$ and $Q_2$ may be $SiR_{13}R_{14}$, and $R_{13}$ and $R_{14}$ may each independently be a substituted or unsubstituted aryl group having 6 to 30 carbon atoms for forming a ring, for example, $R_{13}$ and $R_{14}$ may each independently be a substituted or unsubstituted phenyl group.

The first compound may be at least one selected from the compounds represented in the following Compound Group 2. However, examples of the first compound of the present disclosure are not limited thereto, and the first compound is not specifically limited, so long as it satisfies Equation 1.

Compound Group 2

2-1
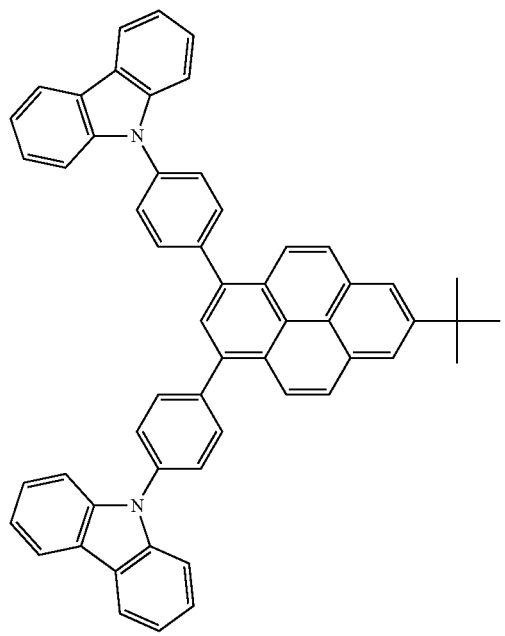

2-2
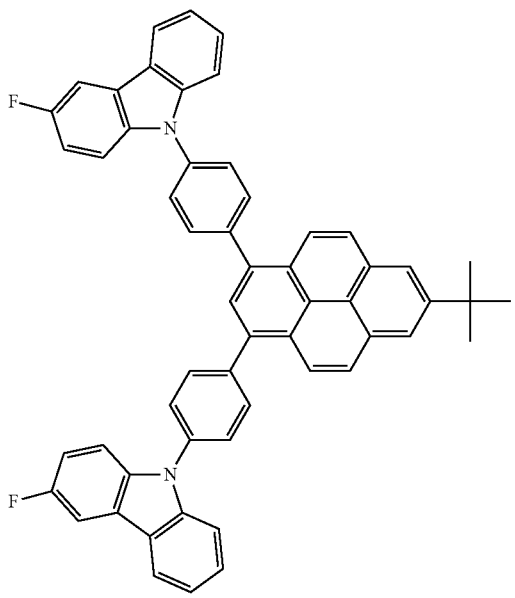

2-3
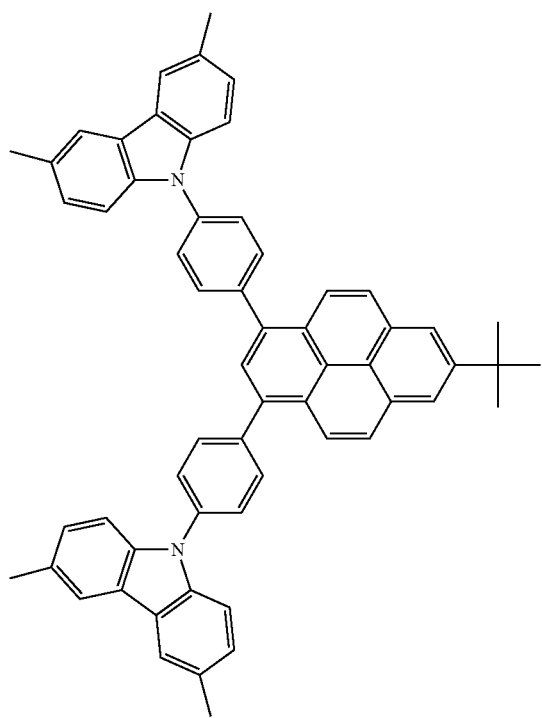

2-4
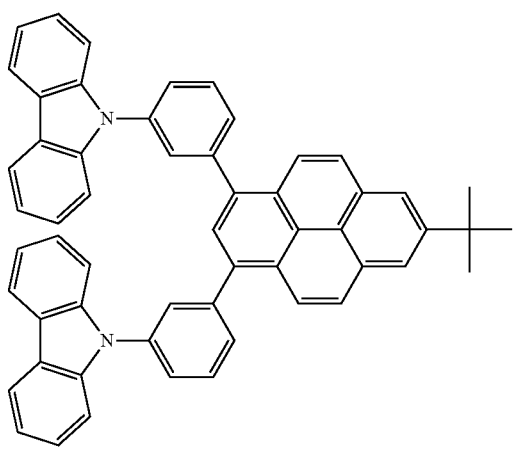

2-5
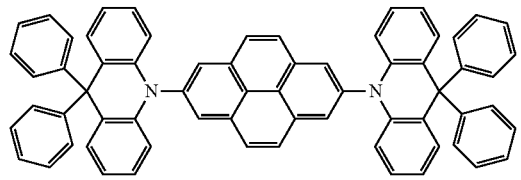
2-6
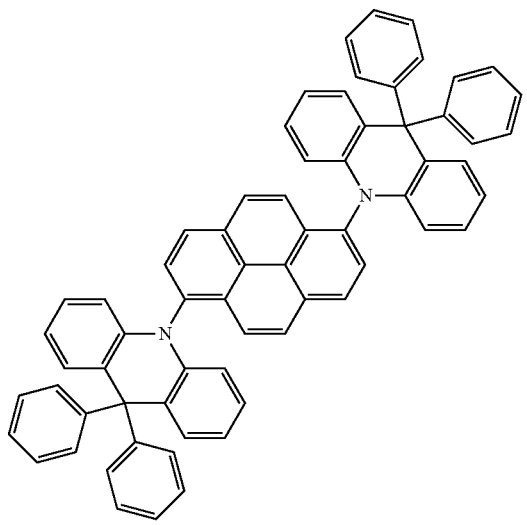
2-7
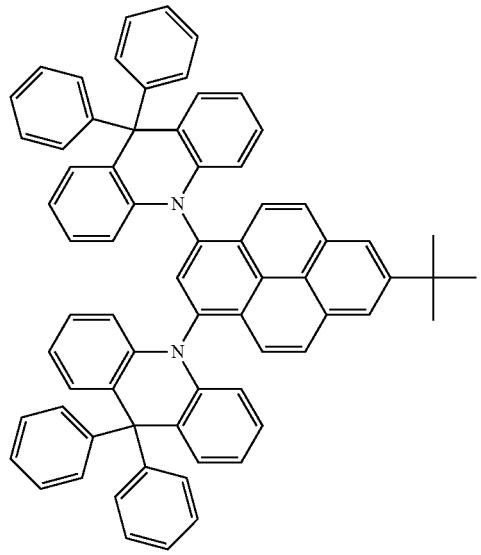
2-8
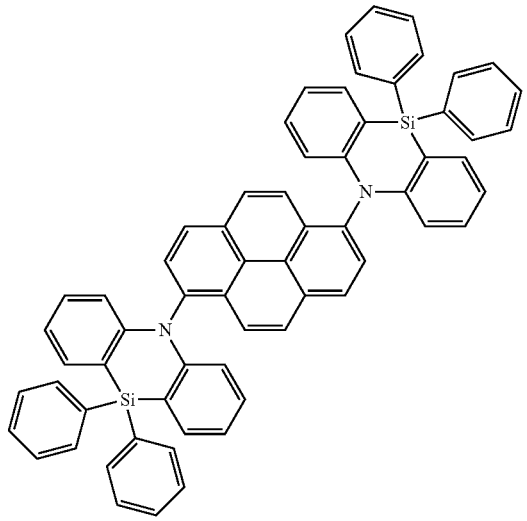
2-9
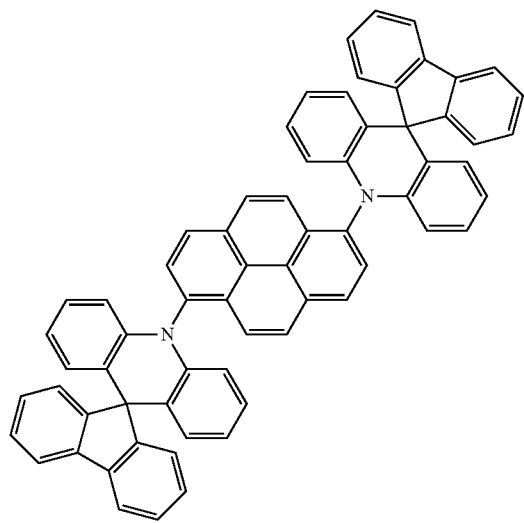
2-10
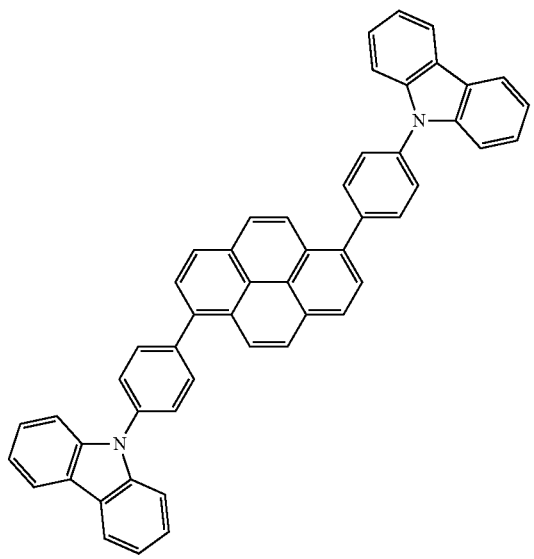

2-11

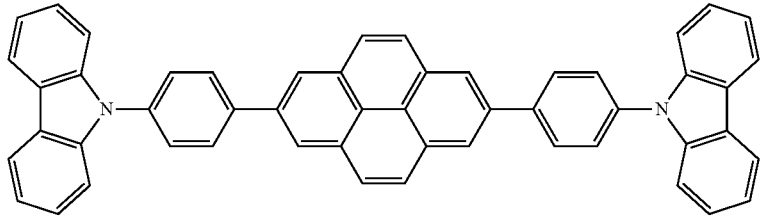

2-12

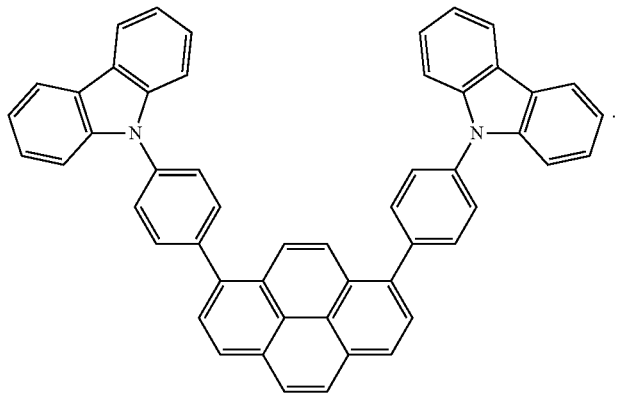

The light emission material according to an embodiment of the present disclosure may be formed using only the first compound. In this case, only one kind (type) of the first compound may be included, or two or more kinds (types) of the first compound may be included.

The light emission material according to an embodiment of the present disclosure may further include a second compound different from the first compound. FIG. 3 is a diagram illustrating a relation between the lowest singlet energy level of a first compound and the lowest triplet energy level of a second compound included in the light emission material according to an embodiment of the present disclosure.

Figure 3:
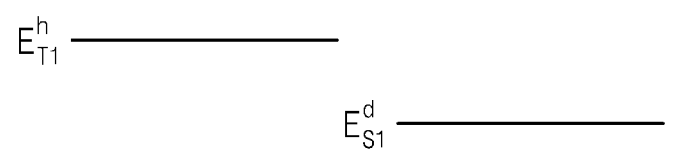

Referring to FIG. 3, the lowest triplet excitation energy level of the second compound ($E^h_{T1}$) may be higher than the lowest singlet excitation energy level of the first compound ($E^d_{S1}$).

In the case where the light emission material according to an embodiment of the present disclosure includes both the first compound and the second compound, the wt % of the second compound may be greater than the wt % of the first compound.

In an embodiment, the light emission material may include at least two kinds (types) of the second compound, and in another embodiment, it may include one kind (type) of the second compound.

The second compound may be represented by, for example, one of the following Formulae 4 to 6. However, an embodiment of the present disclosure is not limited thereto.

Formula 4

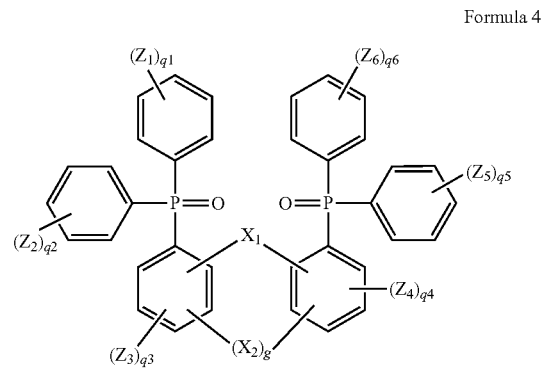

Formula 5

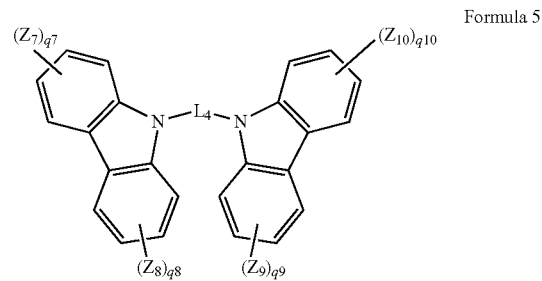

Formula 6

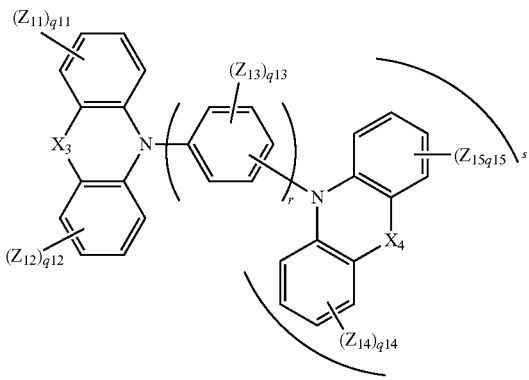

In Formula 4, $X_1$ and $X_2$ may each independently be a direct linkage, O, S, CRaRb or SiRcRd, Ra to Rd and $Z_1$ to $Z_6$ may each independently be hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, g may be 0 or 1, q1, q2, q5 and q6 may each independently be an integer of 0 to 5, and q3 and q4 may each independently be an integer of 0 to 4.

In Formula 4, in the case where q1 is 2 or more, plurality of $Z_1$ may be the same or different. In Formula 2, in the case where q2 is 2 or more, plurality of $Z_2$ may be the same or different. In Formula 2, in the case where q3 is 2 or more, plurality of $Z_3$ may be the same or different. In Formula 2, in the case where q4 is 2 or more, plurality of $Z_4$ may be the same or different. In Formula 2, in the case where q5 is 2 or more, plurality of $Z_5$ may be the same or different. In Formula 2, in the case where q6 is 2 or more, plurality of $Z_6$ may be the same or different.

In Formula 5, $Z_7$ to $Z_{10}$ may each independently be hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, $L_4$ may be a substituted or unsubstituted arylene group having 6 to 30 carbon atoms for forming a ring, or a substituted or unsubstituted heteroarylene group having 2 to 30 carbon atoms for forming a ring, and q7 to q10 may each independently be an integer of 0 to 4.

In Formula 5, in the case where q7 is 2 or more, plurality of $Z_7$ may be the same or different. In Formula 3, in the case where q8 is 2 or more, plurality of $Z_8$ may be the same or different. In Formula 3, in the case where q9 is 2 or more, plurality of $Z_9$ may be the same or different. In Formula 3, in the case where q10 is 2 or more, plurality of $Z_{10}$ may be the same or different.

In Formula 6, $X_3$ and $X_4$ may each independently be O, S, CRaRb or SiRcRd, Ra to Rd and $Z_{11}$ to $Z_{15}$ may each independently be hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, q11 to q15 may each independently be an integer of 0 to 4, s may be 0 or 1, and r may be 1 or 2. In Formula 6, if s is 0, q13 is an integer of 0 to 5.

In Formula 6, in the case where q11 is 2 or more, plurality of $Z_{11}$ may be the same or different. In Formula 6, in the case where q12 is 2 or more, plurality of $Z_{12}$ may be the same or different. In Formula 6, in the case where q13 is 2 or more, plurality of $Z_{13}$ may be the same or different. In Formula 6, in the case where q14 is 2 or more, plurality of $Z_{14}$ may be the same or different. In Formula 6, in the case where q15 is 2 or more, plurality of $Z_{15}$ may be the same or different.

In Formula 4, $X_1$ may be O or S, g may be 1, and $X_2$ may be a direct linkage or CRaRb. In Formula 2, $X_1$ may be O or S, and g may be 0.

In Formula 4, all q1 to q6 may be 0. However, an embodiment of the present disclosure is not limited thereto, and in an embodiment, at least one of q1 to q6 may be 1 or more.

In Formula 4, at least one of $Z_1$ to $Z_6$ may be a substituted or unsubstituted alkyl group having 1 to 10 carbon atoms, or a substituted or unsubstituted aryl group having 6 to 30 carbon atoms for forming a ring. The second compound represented by Formula 4 may be, for example, one of the following compounds, but is not limited thereto.

4-1

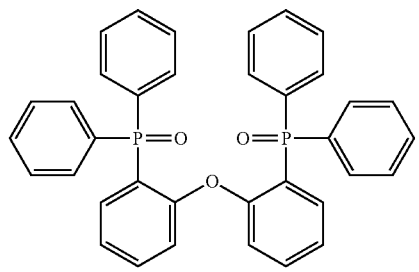

4-2

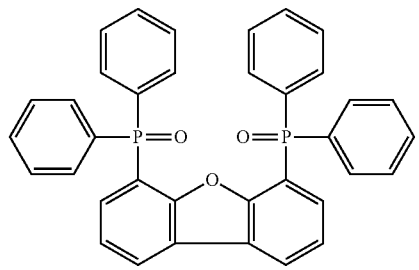

4-3

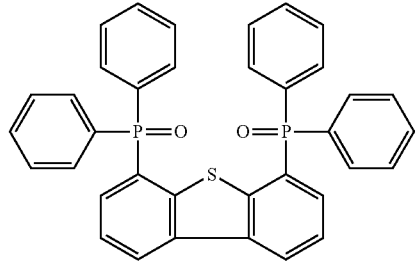

4-4

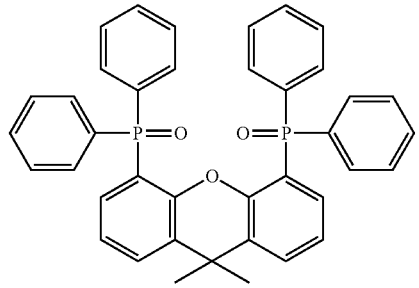

4-5

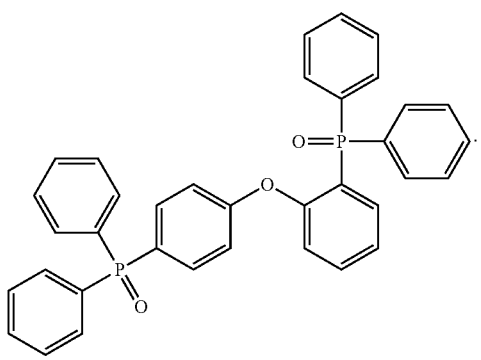

5-3

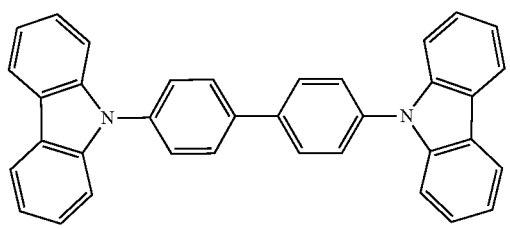

5-4

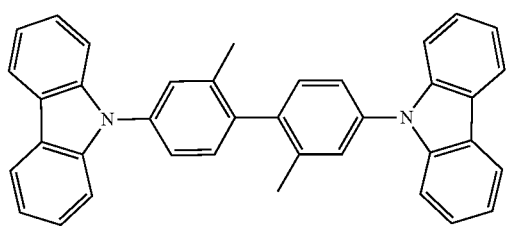

5-5

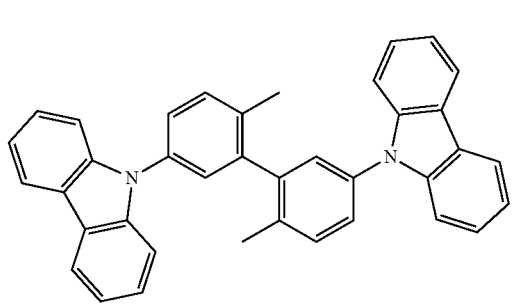

5-6

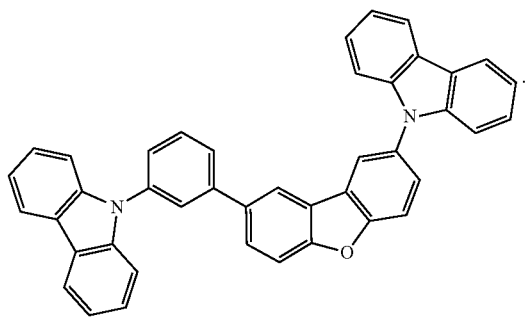

In Formula 5, $L_4$ may be a substituted or unsubstituted arylene group having 6 to 30 carbon atoms for forming a ring. In Formula 5, $L_4$ may be a substituted or unsubstituted arylene group having 6 to 15 carbon atoms for forming a ring. In Formula 5, $L_4$ may be an arylene group having a monocyclic structure. In Formula 5, $L_4$ may be a substituted or unsubstituted phenylene group or a divalent biphenylene group. In Formula 5, $L_4$ may be an arylene group having a polycyclic structure. In Formula 5, $L_4$ may be a divalent naphthalene group.

In Formula 5, all q7 to q10 may be 0. However, an embodiment of the present disclosure is not limited thereto, and in an embodiment, at least one of q7 to q10 may be 1 or more.

In Formula 5, at least one of $Z_7$ to $Z_{10}$ may be a substituted or unsubstituted alkyl group having 1 to 10 carbon atoms, or a substituted or unsubstituted aryl group having 6 to 30 carbon atoms for forming a ring.

The second compound represented by Formula 5 may be, for example, one of the following compounds, but is not limited thereto.

5-1

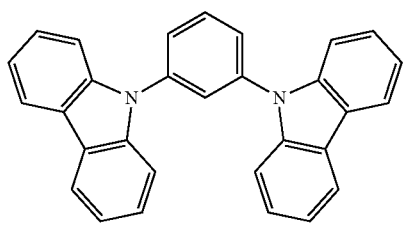

5-2

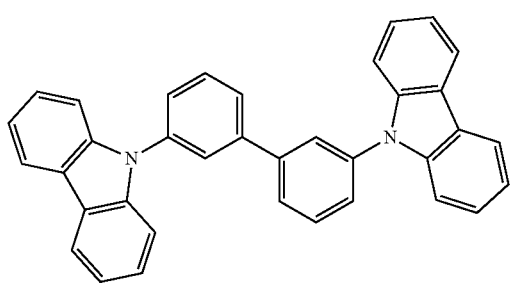

In Formula 6, $X_3$ and $X_4$ may be the same, for example, $X_3$ and $X_4$ may be CRaRb. Ra and Rb may be each independently a substituted or unsubstituted aryl group having 6 to 30 carbon atoms for forming a ring, for example, may be each independently a substituted or unsubstituted phenyl group. In Formula 6, s may be 0, and r may be 1. However, an embodiment of the present disclosure is not limited thereto.

In Formula 6, all q11 to q13 may be 0. However, an embodiment of the present disclosure is not limited thereto, and in an embodiment, at least one of q11 to q13 may be 1 or more.

In Formula 6, at least one of $Z_{11}$ to $Z_{13}$ may be a substituted or unsubstituted alkyl group having 1 to 10 carbon atoms, or a substituted or unsubstituted aryl group having 6 to 30 carbon atoms for forming a ring.

The second compound represented by Formula 6 may be, for example, one of the following compounds.

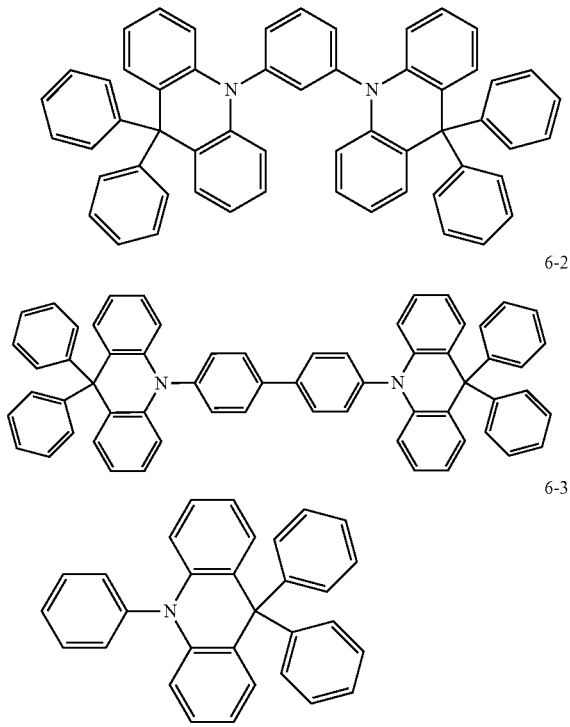

The light emission material according to an embodiment of the present disclosure may have a light emission mechanism based on the transition from a singlet state to a ground state. The light emission material according to an embodiment of the present disclosure may be a fluorescence emission material.

The light emission material according to an embodiment of the present disclosure has good (or suitable) emission efficiency. When the light emission material according to an embodiment of the present disclosure is used in an organic electroluminescence device, high efficiency and the minimization (or reduction) of roll-off phenomenon may be simultaneously (or concurrently) attained.

Hereinafter, an organic electroluminescence device according to another embodiment of the present disclosure will be explained. The following explanation will primarily focus on the differences between the present embodiment and the above-described light emission material, and the portions (or parts) not explained below will be presumed to have the same descriptions as those provided in connection with the light emission material according to an embodiment of the present disclosure described above.

The organic electroluminescence device according to an embodiment of the present disclosure includes the above-described light emission material according to an embodiment of the present invention.

Figure 4:
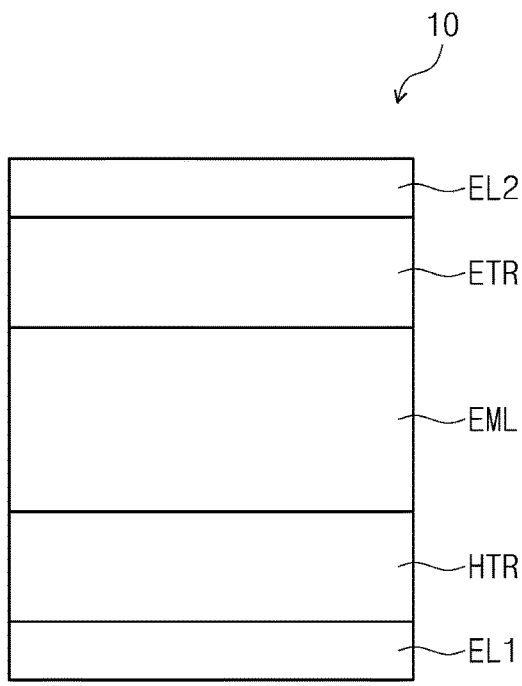
FIG. 4 is a cross-sectional view schematically illustrating an organic electroluminescence device according to an embodiment of the present disclosure.
Figure 5:
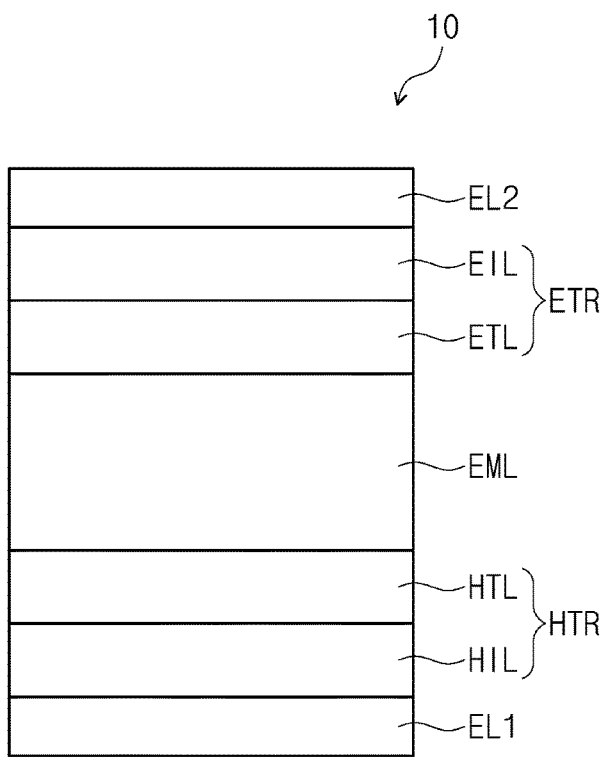
FIG. 5 is a cross-sectional view schematically illustrating an organic electroluminescence device according to an embodiment of the present disclosure.

FIG. 4 is a cross-sectional view schematically illustrating an organic electroluminescence device according to an embodiment of the present disclosure. FIG. 5 is a cross-sectional view schematically illustrating an organic electroluminescence device according to an embodiment of the present disclosure.

Referring to FIGS. 4 and 5, an organic electroluminescence device 10 according to an embodiment of the present disclosure includes a first electrode EL1, a hole transport region HTR, an emission layer EML, an electron transport region ETR, and a second electrode EL2.

The first electrode EL1 has conductivity. The first electrode EL1 may be a pixel electrode or an anode. The first electrode EL1 may be a transmissive electrode, a transflective electrode, or a reflective electrode. In the case where the first electrode EL1 is the transmissive electrode, the first electrode EL1 may include a transparent metal oxide such as indium tin oxide (ITO), indium zinc oxide (IZO), zinc oxide (ZnO), and/or indium tin zinc oxide (ITZO). In the case where the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EU may include a plurality of layers including a reflective layer and/or a transflective layer formed using the above materials, and a transmissive layer formed using ITO, IZO, ZnO, and/or ITZO.

The hole transport region HTR is provided on the first electrode EL1. The hole transport region HTR may include at least one of a hole injection layer HIL, a hole transport layer HTL, a hole buffer layer, and an electron blocking layer. The thickness of the hole transport region HTR may be, for example, from about 500 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material. Alternatively, the hole transport region HTR may have a single layer structure formed using a plurality of different materials, or a structure (laminated from the first electrode EU1) of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation.

The hole transport region HTR may be formed using any suitable method such as a vacuum deposition method, a spin coating method, a cast method, a Langmuir-Blodgett (LB) method, an inkjet printing method, a laser printing method, and/or a laser induced thermal imaging (LITI) method.

The hole injection layer HIL may include, for example, a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{(N-2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), or polyaniline/poly(4-styrenesulfonate) (PANI/PSS), N,N'-di(naphthalene-1-yl)-N,N'-diphenyl-benzidine (α-NPD), triphenylamine-containing polyetherketone (TPAPEK), 4-isopropyl-4'-methyldiphenyliodonium tetrakis(pentafluorophenyl)borate, dipyrazino[2,3-f:2',3'-h]quinoxaline-2,3,6,7,10,11-hexacarbonitrile (HAT-CN), etc.

The hole transport layer HTL may include, for example, carbazole derivatives (such as N-phenyl carbazole and/or polyvinyl carbazole), fluorine-based derivatives, triphenylamine-based derivatives (such as N,N'-bis(3-methylphenyl)-N,N'-diphenyl-[1,1-biphenyl]-4,4'-diamine (TPD) and/or 4,4',4"-tris(N-carbazolyl)triphenylamine (TCTA)), N,N'-di(naphthalene-1-yl)-N,N'-diphenyl-benzidine (α-NPD), 4,4'-cyclohexylidene bis[N,N-bis(4-methylphenyl)benzenamine]) (TAPC), 4,4'-bis[N,N'-(3-tolyl) amino]-3,3'-dimethylbiphenyl (HMTPD), etc.

The thickness of the hole transport region HTR may be from about 100 Å to about 10,000 Å, for example, from about 100 Å to about 1,000 Å. In the case where the hole transport region HTR includes both the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. In the case where the thicknesses of the hole transport region HTR, the hole injection layer HIL, and the hole transport layer HTL satisfy the above-described ranges, satisfactory (or suitable) hole transport properties may be obtained without substantial increase of a driving voltage.

The hole transport region HTR may further include a charge generating material in addition to the above-described materials, to improve conductivity. The charge generating material may be dispersed uniformly or non-uniformly in the hole transport region HTR. The charge generating material may be, for example, a p-dopant. The p-dopant may be one selected from a quinone derivative, a metal oxide, and a cyano group-containing compound, without limitation. Non-limiting examples of the p-dopant may include quinone derivatives such as tetracyanoquinodimethane (TCNQ) and/or 2,3,5,6-tetrafluoro-tetracyanoquinodimethane (F4-TCNQ), and metal oxides such as tungsten oxide and/or molybdenum oxide, without limitation.

As described above, the hole transport region HTR may further include at least one of a hole buffer layer and an electron blocking layer, in addition to the hole injection layer HIL and the hole transport layer HTL. The hole buffer layer may compensate an optical resonance distance according to the wavelength of light emitted from the emission layer EML and increase light emission efficiency. Any of the suitable materials included in the hole transport region HTR may be used as materials included in the hole buffer layer. The electron blocking layer is a layer which plays the role of preventing (or reducing) the electron injection from the electron transport region ETR (e.g., from the second electrode) into the hole transport region HTR.

The emission layer EML is provided on the hole transport region HTR. The thickness of the emission layer EML may be, for example, from about 100 Å to about 300 Å. The emission layer EML may have a single layer formed using a single material, a single layer formed using a plurality of different materials, or a multilayer structure having a plurality of layers formed using a plurality of different materials.

The emission layer EML includes above-described light emission material including the first compound according to an embodiment of the present disclosure.

The emission layer EML may be an emission layer composed of only one kind (type) of the first compound, or an emission layer composed of at least two kinds (types) of the first compound. The emission layer EML may be an emission layer composed of a light emission material including both the first compound and the second compound. In this case, only one kind (type) of the second compound may be included, or at least two kinds (types) of the second compound may be included.

The emission layer EML may be a fluorescence emission layer. A fluorescence emission layer may refer to a layer in which a light emission material emits light via a fluorescence mechanism.

The emission layer EML may be a blue emission layer. The emission layer EML may emit light having a maximum emission wavelength of about 480 nm or less. For example, the emission layer EML may emit blue light in a wavelength region of about 430 nm to about 480 nm.

The emission layer EML may include a host and a dopant. Referring to FIG. 3 again, the emission layer EML preferably includes a host having the lowest triplet excitation energy level ($E^h_T1$) that is higher than the lowest singlet excitation energy level ($E^d_{S1}$) of the dopant. In this case, efficiency reduction due to reverse energy transfer from the dopant to the host may be minimized or reduced.

The dopant of the emission layer EML may be the first compound.

The host of the emission layer EML may be the second compound. However, an embodiment of the present disclosure is not limited thereto, and the emission layer EML may include any suitable host material in the technical field.

The emission layer EML may have a thickness of about 100 Å to about 1,000 Å.

Referring to FIGS. 5 and 6 again, the electron transport region ETR is provided on the emission layer EML. The electron transport region ETR may include at least one of an electron blocking layer, an electron transport layer ETL and an electron injection layer EIL, without limitation.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of the electron injection layer EIL or the electron transport layer ETL, or a single layer structure formed using an electron injection material and an electron transport material. In some embodiments, the electron transport region ETR may have a single layer structure formed using a plurality of different materials, or a structure (laminated from the first electrode EL1) of electron transport layer ETL/electron injection layer EIL, or hole blocking layer/electron transport layer ETL/electron injection layer EIL, without limitation. The thickness of the electron transport region ETR may be, for example, from about 1,000 Å to about 1,500 Å.

The electron transport region ETR may be formed using any suitable method such as a vacuum deposition method, a spin coating method, a cast method, a Langmuir-Blodgett (LB) method, an inkjet printing method, a laser printing method, and/or a laser induced thermal imaging (LITI) method.

In the case where the electron transport region ETR includes the electron transport layer ETL, the electron transport region ETR may include tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)

aluminum (BAlq), berylliumbis(benzoquinolin-10-olate (Bebq2), 9,10-di(naphthalene-2-yl)anthracene (ADN), or a mixture thereof, without limitation. The thickness of the electron transport layer ETL may be from about 100 Å to about 1,000 Å, and may be from about 150 Å to about 500 Å. If the thickness of the electron transport layer ETL satisfies the above-described range, satisfactory (or suitable) electron transport properties may be obtained without substantial increase of a driving voltage.

When the electron transport region ETR includes the electron injection layer EIL, the electron transport region ETR may include LiF, lithium quinolate (LiQ), $Li_2O$, BaO, NaCl, CsF, a metal in lanthanoides such as Yb, and/or a metal halide such as RbCl and/or RbI. However, an embodiment of the present disclosure is not limited thereto. The electron injection layer EIL also may be formed using a mixture material of an electron transport material and an insulating organo-metal salt. The organo-metal salt may be a material having an energy band gap of about 4 eV or more. The organo-metal salt may include, for example, metal acetates, metal benzoates, metal acetoacetates, metal acetylacetonates, and/or metal stearates. The thickness of the electron injection layer EIL may be from about 1 Å to about 100 Å, and may be from about 3 Å to about 90 Å. In the case where the thickness of the electron injection layer EIL satisfies the above described range, satisfactory (or suitable) electron injection properties may be obtained without inducing the substantial increase of a driving voltage.

The electron transport region ETR may include a hole blocking layer, as described above. The hole blocking layer may include, for example, at least one of bis{2-[di(phenyl) phosphino]phenyl}ether oxide (DPEPO), 2,9-dimethyl-4,7-diphenyl-1,10-phenanthroline (BCP), and 4,7-diphenyl-1,10-phenanthroline (Bphen). However, an embodiment of the present disclosure is not limited thereto.

The second electrode EL2 is provided on the electron transport region ETR. The second electrode EL2 may be a common electrode or a cathode. The second electrode EL2 may be a transmissive electrode, a transflective electrode or a reflective electrode. In the case where the second electrode EL2 is the transmissive electrode, the second electrode EL2 may include a transparent metal oxide, for example, ITO, IZO, ZnO, ITZO, etc.

In the case where the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer and/or a transflective layer formed using any of the above-described materials, and a transparent conductive layer formed using ITO, IZO, ZnO, and/or ITZO, etc.

The second electrode EL2 may be connected to an auxiliary electrode. In the case where the second electrode EL2 is connected to the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via the relaxation from an excited state to a ground state.

In the case where the organic electroluminescence device 10 is a top emission type (e.g., top emission organic electroluminescence device), the first electrode EU may be a reflective electrode and the second electrode EL2 may be a transmissive electrode or a transflective electrode. In the case where the organic electroluminescence device 10 is a bottom emission type (e.g., bottom emission organic electroluminescence device), the first electrode EU may be a transmissive electrode or a transflective electrode and the second electrode EL2 may be a reflective electrode.

The organic electroluminescence device according to an embodiment of the present disclosure may include a fluorescence emission layer and may have a maximum external quantum yield of about 5% or more.

The organic electroluminescence device according to an embodiment of the present disclosure may include the light emission material according to an embodiment of the present disclosure, thereby attaining high efficiency and roll-off reduction phenomenon at the same time. For example, the organic electroluminescence device according to an embodiment of the present disclosure including the light emission material may exhibit a maximum external quantum yield of greater than about 5%, which has been regarded as the limitation of fluorescence emission, and thus the thermal energy required by a light emission material for light emission is zero or extremely small, thereby decreasing the possibility of a roll-off phenomenon.

Hereinafter the present disclosure will be explained in more detail with reference to specific examples and comparative examples. The following examples are only illustrations designed to assist the understanding of the present disclosure, and the scope of the present disclosure is not limited thereto.

SYNTHETIC EXAMPLES

The first compound included in the light emission material according to an embodiment of the present disclosure was synthesized, for example, as follows. However, the synthetic method is not limited thereto.

1. Synthesis of Compound 1-1

8.13 g of 4-(carbazol-9-yl)benzaldehyde, and 5.67 g of p-xylylenediphosphonic acid tetraethyl ester were dissolved in 250 ml of a THF solvent, and while stirring, a THF solution of 0.05 M tert-potassium butoxide was added drop-wise at room temperature for about 6 hours. Produced precipitate was filtered and washed with 100 ml of water and 300 ml of ethanol in order to obtain 7.75 g (yield 84%) of a yellow compound. FAB-MS (Fast Atom Bombardment—Mass Spectrometry) analysis result of the yellow compound thus produced is as follows:

M/z 612 (M+), 613 (MH+)

From the foregoing analysis result, the yellow compound was identified as Compound 1-1.

2. Synthesis of Compound 1-4

The same (or substantially the same) synthetic method as the one used for Compound 1-1 was conducted, except for using 8.69 g of 4-(3-fluorocarbazol-9-yl)benzaldehyde instead of 4-(carbazol-9-yl)benzaldehyde to obtain 7.70 g (yield 80%) of a yellow compound. FAB-MS analysis result of the yellow compound thus produced is as follows:

M/z 648 (M+), 649 (MH+)

From the foregoing analysis result, the yellow compound was identified as Compound 1-4.

3. Synthesis of Compound 1-14

Under an argon (Ar) atmosphere, to 3.27 g of 9H-carbazole, 3.0 g of 4,4"-dibromostilbene, 0.56 g of palladium(0) bis(dibenzylideneacetone), and 5.11 g of sodium-tert-butoxide, 30 ml of toluene and 0.7 ml of a toluene solution of 2M tri(tert-butyl)phosphine were added in order, followed by heating and refluxing the resulting mixture for about 5 hours. The reaction product was cooled to room temperature, and the precipitated crystal (precipitate) was filtered and washed with 50 ml of water and 100 ml of ethanol in order to obtain 3 g (yield 61%) of a yellow compound. FAB-MS analysis result of the yellow compound thus produced is as follows:

M/z 551 (M+), 552 (MH+)

From the foregoing analysis result, the yellow compound was identified as Compound 1-14.

4. Synthesis of Compound 2-1

1.6 g of 4-(9-carbazolyl)phenylboronic acid, 1.13 g of 1,3-dibromo-7-tert-butylpyrene, 0.35 g of tetrakis(triphenylphosphine)palladium(0), 2.5 g of potassium phosphate, 10 ml of water, and 150 ml of THF were refluxed for about 12 hours, and then stood until the temperature reached room temperature. Precipitated crystal (precipitate) was filtered, washed with ethanol, water and acetone one by one, and dried to obtain 1.2 g (yield 48%) of a lemon yellow crystal (solid). FAB-MS analysis result of the lemon yellow compound thus produced is as follows:

M/z 740.3 (M+), 741.3 (MH+)

Experimental Example 1

The lowest singlet excitation state energy, n-th triplet excitation state energy and off-diagonal vibronic coupling constant with respect to a triplet excitation state energy level of Compounds 1-1, 1-4 and 1-14 and the following Comparative Compounds C-1 and C-2 are summarized and listed in Table 1 below. In the following Table 1, the maximum external quantum yield of a device including each compound in an emission layer is also shown.

The calculation method followed Gaussian09, the calculation of the excitation energy level was conducted according to B3LYP/6-31G(d), and the off-diagonal vibronic coupling constant Vn was obtained according to a method described in Phys. Chem. Chem. Phys. 16, 14244-14256 (2014) (Sato et al.).

In Energy may refer to an energy level of triplet state which enhances fluorescence (e.g., n-th triplet excitation state energy), and Vn may refer to an off-diagonal vibronic coupling constant of triplet state which enhances fluorescence.

Experimental Example 2

Organic electroluminescence devices according to Examples 1 to 3 were manufactured using Compounds 1-1, 1-4 and 1-14, respectively, as the dopant materials of an emission layer. An organic electroluminescence device of Comparative Example 1 was manufactured by the same method as in Example 1 (described below), except for using a different host material. Organic electroluminescence devices of Comparative Examples 2 to 4 were manufactured using the following Compound TBPe, and Comparative Compounds C-1 and C-2, respectively.

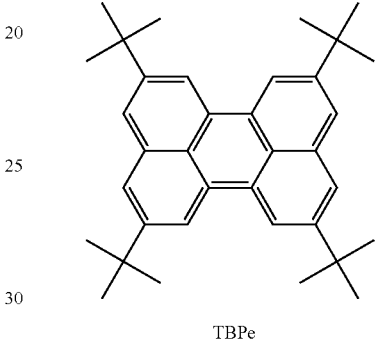

TBPe

The organic electroluminescence devices of Examples 1 to 3 and Comparative Examples 1 to 4 were manufactured as follows.

A first electrode was formed using ITO to a thickness of about 150 nm, a hole injection layer was formed using dipyrazino[2,3-f:2',3'-h]quinoxaline-2,3,6,7,10,11-hexacarbonitrile (HAT-CN) to a thickness of about 10 nm, a hole transport layer was formed using α-NPD to a thickness of about 80 nm, an electron blocking layer was formed using mCP to a thickness of about 5 nm, an emission layer doped with x % (see Table 2 for specific %) of a dopant (see Table 2 for specific dopants) was formed to a thickness of about 20 nm, a hole blocking layer was formed using bis{2-[di

TABLE 1

Comparative Compounds

| Compound | S1 Energy (eV) | Tn Energy (eV) | Off-diagonal vibronic coupling constant Vn (a.u.) | Maximum external quantum yield (%) |
|---|---|---|---|---|
| 1-1 | 2.79 | T4:2.88 | $2 \times 10^{-5}$ | 6.3 |
| 1-4 | 2.78 | T4:2.88 | $2 \times 10^{-5}$ | 6.3 |
| 1-14 | 3.08 | T3:2.88 | $4 \times 10^{-5}$ | 5.5 |
| C1 | 3.25 | T3:3.39 | $4 \times 10^{-4}$ | 2.5 |
| C2 | 2.91 | T3:3.08 | $2 \times 10^{-4}$ | 4.3 |

(phenyl) phosphino]phenyl}ether oxide (DPEPO and ADN (in Comparative Example 1)) to a thickness of about 10 nm, an electron transport layer was formed using 1,3,5-tris(1-phenyl-1H-benzimidazol-2-yl) benzene (TPBi) to a thickness of about 30 nm, an electron injection layer was formed using lithium fluoride (LiF) to a thickness of about 0.5 nm, and a second electrode was formed using Al to a thickness of about 100 nm. Each layer and the second electrode were formed by a vacuum deposition method. In addition, a brightness light distribution characteristics measurement system of C9920-11 by HAMAMATSU Photonics Co., was used for the evaluation of light emission properties of the organic EL devices thus manufactured.

TABLE 2

| Device manufacturing example | Host | Host (x %) | Driving voltage (V, 10 mA/cm$^2$) | Maximum external quantum efficiency (%) |
|---|---|---|---|---|
| Example 1 | DPEPO | Compound 1-1 (25%) | 6.3 | 6.3 |
| Example 2 | DPEPO | Compound 1-4 (24%) | 6.0 | 6.3 |
| Example 3 | DPEPO | Compound 1-14 (25%) | 6.2 | 5.5 |
| Comparative Example 1 | ADN | Compound 1-1 (6%) | 4 | 3.2 |
| Comparative Example 2 | DPEPO | TBPe (25%) | 9 | 0.4 |
| Comparative Example 3 | DPEPO | C1 (12%) | 8.2 | 2.5 |
| Comparative Example 4 | DPEPO | C2 (6%) | 7.3 | 4.3 |

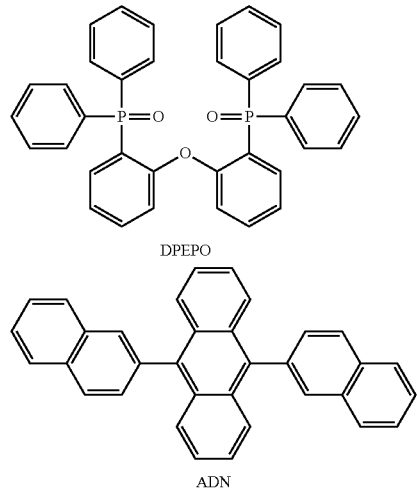

DPEPO

ADN

The lowest triplet excitation state energy (T1) of the host was obtained by measuring phosphorescence emission spectrum at a low temperature, and the lowest singlet excitation state energy (S1) of the dopant was obtained by measuring fluorescence emission spectrum at room temperature. The energy values were: DPEPO (T1 3.6 eV), ADN (T1 2.6 eV), Compound 1 (S1 3.0 eV), and TBPe (S1 2.83 eV).

Referring to Table 2, it was found that the maximum external quantum efficiency of Examples 1 to 3 was about 5% or more. Since the off-diagonal vibronic coupling constant (Vn) between an n-th triplet excitation state and the lowest triplet excitation state is small, inactivation by heat in an n-th triplet excitation state might be difficult to occur, and thus light is emitted by reverse intersystem crossing from an n-th triplet excitation state to an adjacent singlet excitation state (ex: the lowest singlet excitation state).

When comparing Example 1 and Comparative Example 1, the lowest triplet excitation energy level of a host is preferably higher than the lowest singlet excitation energy level of a dopant. For example, when in Comparative Example 1, a host having the lowest triplet excitation energy level (2.6 eV) lower than the lowest singlet excitation energy level of Compound 1-1 (3.0 eV) was used, the maximum external quantum efficiency was markedly decreased when compared to that of Example 1.

In Examples 1 to 3, delayed light emission was not observed, and it was found that the light emission material according to an embodiment of the present disclosure is not an emission material of thermally activated delayed fluorescence. In addition, in Examples 1 to 3, delayed light emission was not observed in a transient organic electroluminescence device experiment, and it was found that the organic electroluminescence device including the light emission material according to an embodiment of the present disclosure is not an emission material of triplet-triplet annihilation (TTA).

The organic electroluminescence device including the light emission material according to an embodiment of the present disclosure may attain a fluorescence emission device having a maximum external quantum efficiency of about 5% or more and may simultaneously (or concurrently) reduce or minimize roll-off phenomenon.

The light emission material according to an embodiment of the present disclosure may have excellent emission efficiency.

The light emission material according to an embodiment of the present disclosure requires extremely (relatively) small heat energy during the transformation from a triplet to a singlet, and when the material is applied in an organic electroluminescence device, the generation ratio of roll-off phenomenon may be minimized or reduced.

The organic electroluminescence device according to an embodiment of the present disclosure may simultaneously (or concurrently) attain high efficiency and roll-off reduction.

Expressions such as "at least one of," "one of," and "selected from," when preceding a list of elements, modify the entire list of elements and do not modify the individual elements of the list. Further, the use of "may" when describing embodiments of the present invention refers to "one or more embodiments of the present invention."

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present invention have been described, it is understood that the present invention should not be limited to these example embodi-

What is claimed is:

1. A light emission material comprising a first compound satisfying the following Equation 1:

$$K2 \geq 0.1 K1, \quad \text{Equation 1}$$

wherein K1 is a sum of radiationless transition rate due to internal conversion from an n-th triplet excitation state to a lower order triplet excitation state including the lowest triplet excitation state, and K2 is a reverse intersystem crossing transition rate from the n-th triplet excitation state to a singlet excitation state, which is adjacent to the n-th triplet excitation state, n is an integer of 2 or more, and the first compound is represented by Formula 1:

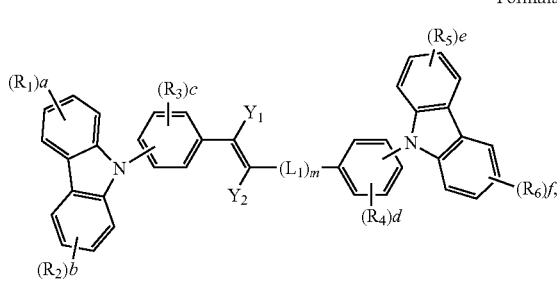

Formula 1 wherein $L_1$ is a divalent substituted or unsubstituted alkenyl group having 2 to 10 carbon atoms, or a substituted or unsubstituted arylene group having 6 to 30 carbon atoms for forming a ring, m is an integer of 0 to 3, wherein when m is 2 or more, a plurality of $L_1$ are the same or different, $R_1$ to $R_6$ are each independently selected from deuterium, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, and a substituted or unsubstituted heteroaryl group having 2 to 30 carbon atoms for forming a ring, $Y_1$ and $Y_2$ are each independently selected from hydrogen, deuterium, a substituted or unsubstituted alkyl group having 1 to 10 carbon atoms, a substituted or unsubstituted aryl group having 6 to 30 carbon atoms for forming a ring, and a substituted or unsubstituted heteroaryl group having 2 to 30 carbon atoms for forming a ring, and a to f are each independently an integer of 0 to 4, provided that:

$R_1$ to $R_6$ are each independently not a t-butyl group, when $R_1$, $R_2$, $R_5$, and $R_6$ are each a bromine atom, then m is an integer of 1 to 3, when a to f are each 0, then m is an integer of 1 to 3, when a to f are each 0, then $(L_1)_m$ does not include a divalent biphenylene group and a divalent ethylene group, when a to f are each 0 and m is 2, then $(L_1)_m$ does not include a divalent unsubstituted phenylene group and a divalent unsubstituted ethylene group, when m is 0, a case where a, b, e, and f are each 1 is excluded, and $R_1$, $R_2$, $R_5$, and $R_6$ are each independently a triphenylsilyl group, and when m is an integer of 1 to 3, at least one of $R_1$, $R_2$, $R_5$, or $R_6$ is a halogen atom, a cyano group, or a substituted or unsubstituted silyl group, or any of a, b, e, or d are each independently an integer of 2 to 4, or at least one of $Y_1$ or $Y_2$ is not hydrogen, and when one of $Y_1$ or $Y_2$ is hydrogen, the remaining one of $Y_1$ or $Y_2$ is not an unsubstituted phenyl group or an unsubstituted methyl group.

2. The light emission material of claim 1, wherein K1 is $1 \times 10^9$ $s^{-1}$ or less.

3. The light emission material of claim 1, wherein the first compound further satisfies the following Equation 2:

$$Vn < 1.5 \times 10^{-4} \text{ (atomic unit)}, \quad \text{Equation 2}$$

wherein Vn is defined with respect to the n-th triplet excitation state and is a maximum value among off-diagonal vibronic coupling constants against each standard vibration mode calculated by quantum chemical calculation between the n-th triplet excitation state and the lowest triplet excitation state.

4. The light emission material of claim 1, wherein a maximum light emission wavelength is 480 nm or less.

5. The light emission material of claim 1, wherein the first compound is at least one selected from compounds represented in the following Compound Group 1:

Compound Group 1

1-4

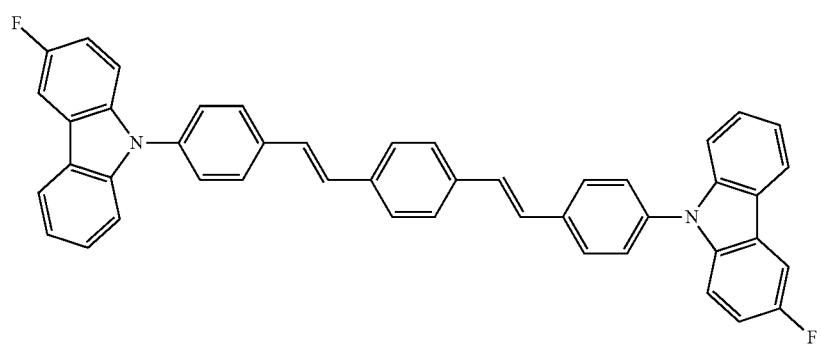

-continued
1-5
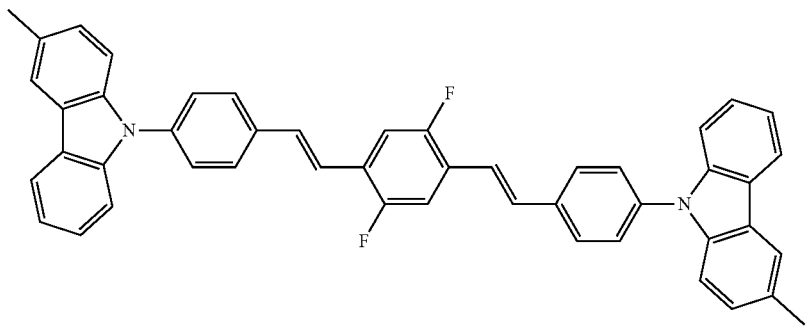
1-8
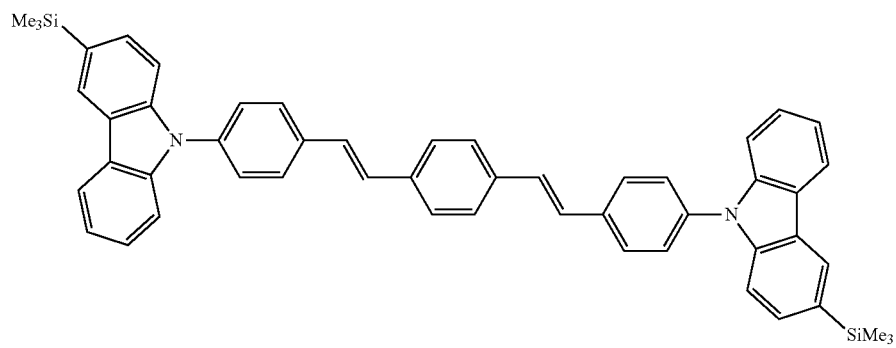
1-9
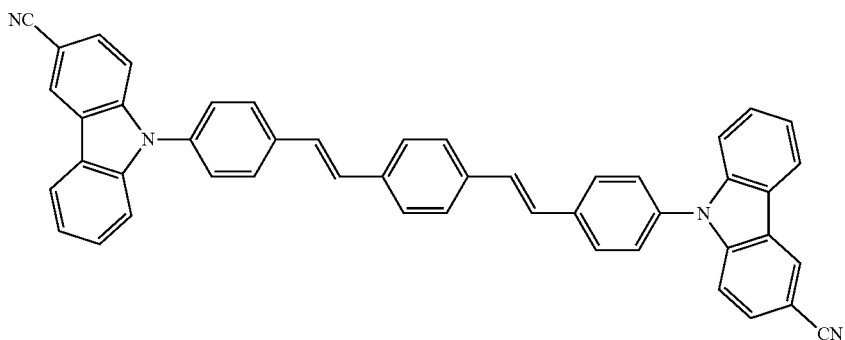
1-10
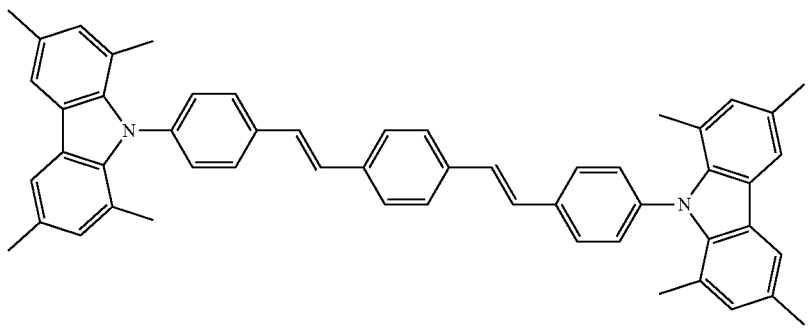
1-12 1-18
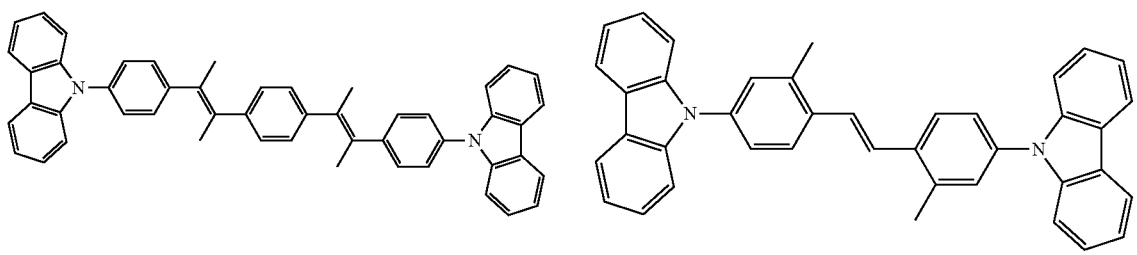

-continued 1-20

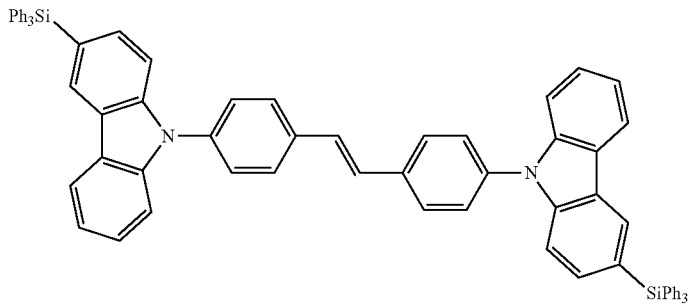

1-28

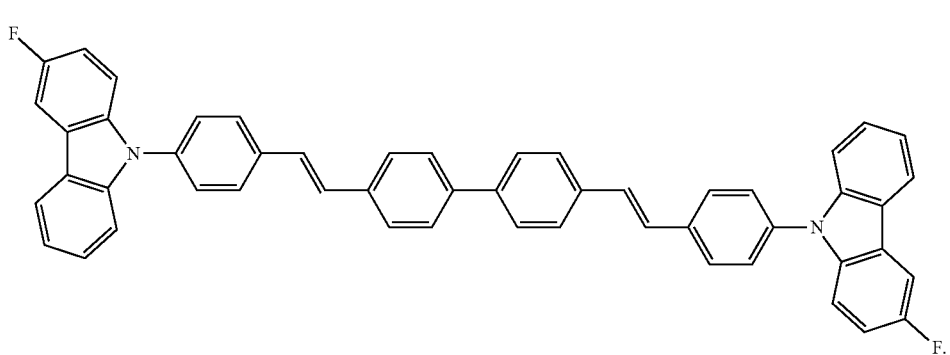

6. The light emission material of claim 1, further comprising a second compound, wherein the lowest triplet excitation energy level of the second compound is higher than the lowest singlet excitation energy level of the first compound.

7. The light emission material of claim 6, wherein the second compound is represented by one of the following Formulae 4 to 6:

Formula 4

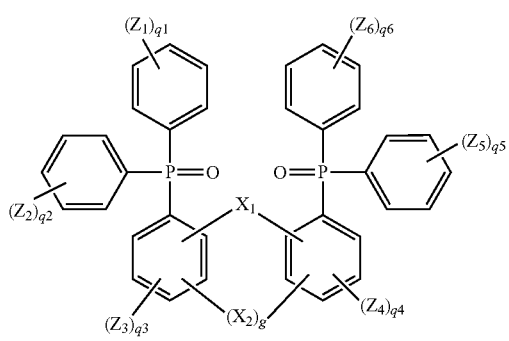

-continued

Formula 5

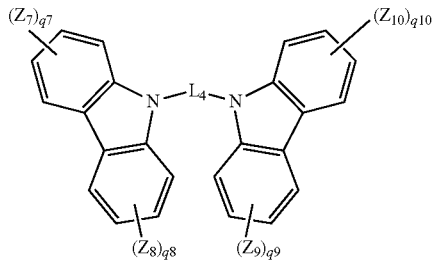

Formula 6

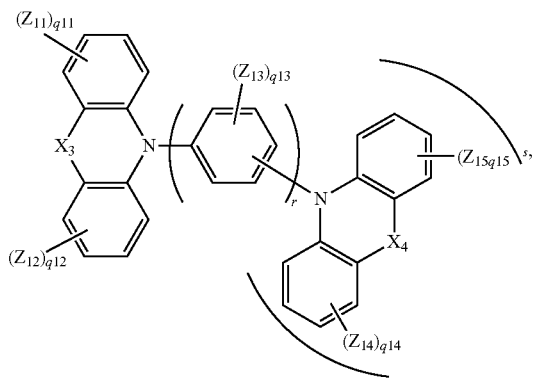

wherein $X_1$ to $X_4$ are each independently a direct linkage, O, S, CRaRb, or SiRcRd, Ra to Rd and $Z_1$ to $Z_{15}$ are each independently selected from hydrogen, deuterium, a halogen atom, a substituted or unsubstituted alkyl group having 1 to 20 carbon atoms, a substituted or unsubstituted aryl group having 6 to 30 carbon atoms for forming a ring, and a substituted or unsubstituted heteroaryl group having 2 to 30 carbon atoms for forming a ring, g and s are each independently 0 or 1, r is 1 or 2, $q_1$, $q_2$, $q_5$, $q_6$ and $q_{13}$ are each independently an integer of 0 to 5;

$q_3$, $q_4$, $q_7$ to $q_{12}$, $q_{14}$ and $q_{15}$ are each independently an integer of 0 to 4, and $L_4$ is a substituted or unsubstituted arylene group having 6 to 30 carbon atoms for forming a ring, or a substituted or unsubstituted heteroarylene group having 2 to 30 carbon atoms for forming a ring.

8. The light emission material of claim 1, having a light emission mechanism based on transition from a singlet state to a ground state.

9. An organic electroluminescence device, comprising:
a first electrode;
a hole transport region on the first electrode;
an emission layer on the hole transport region;
an electron transport region on the emission layer; and
a second electrode on the electron transport region,
wherein the emission layer comprises a first compound satisfying the following Equation 1:

$$K2 \geq 0.1 K1, \quad \text{Equation 1}$$

wherein K1 is a sum of radiationless transition rate due to internal conversion from an n-th triplet excitation state to a lower order triplet excitation state including the lowest triplet excitation state, K2 is a reverse intersystem crossing transition rate from the n-th triplet excitation state to a singlet excitation state adjacent to the n-th triplet excitation state, and n is an integer of 2 or more, and the first compound is represented by Formula 1:

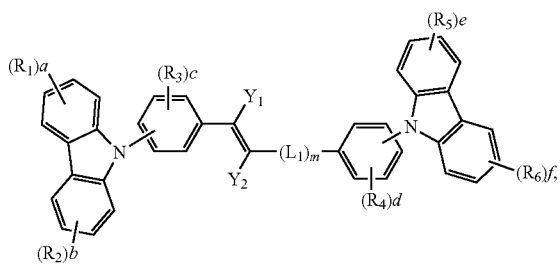

Formula 1 wherein $L_1$ is a divalent substituted or unsubstituted alkenyl group having 2 to 10 carbon atoms, or a substituted or unsubstituted arylene group having 6 to 30 carbon atoms for forming a ring, m is an integer of 0 to 3, wherein when m is 2 or more, a plurality of Li are the same or different, $R_1$ to $R_6$ are each independently selected from deuterium, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, and a substituted or unsubstituted heteroaryl group having 2 to 30 carbon atoms for forming a ring, $Y_1$ and $Y_2$ are each independently selected from hydrogen, deuterium, a substituted or unsubstituted alkyl group having 1 to 10 carbon atoms, a substituted or unsubstituted aryl group having 6 to 30 carbon atoms for forming a ring, and a substituted or unsubstituted heteroaryl group having 2 to 30 carbon atoms for forming a ring, and a to f are each independently an integer of 0 to 4, provided that:

$R_1$ to $R_6$ are each independently not a t-butyl group, when $R_1$, $R_2$, $R_5$, and $R_6$ are each a bromine atom, then m is an integer of 1 to 3, when a to f are each 0, then m is an integer of 1 to 3, when a to f are each 0, then $(L_1)_m$ does not include a divalent biphenylene group and a divalent ethylene group, when a to f are each 0 and m is 2, then $(L_1)_m$ does not include a divalent unsubstituted phenylene group and a divalent unsubstituted ethylene group, when m is 0,
  a case where a, b, e, and f are each 1 is excluded, and
  $R_1$, $R_2$, $R_5$, and $R_6$ are each independently a triphenylsilyl group, and when m is an integer of 1 to 3,
  at least one of $R_1$, $R_2$, $R_5$, or $R_6$ is a halogen atom, a cyano group, or a substituted or unsubstituted silyl group, or
  any of a, b, e, or d are each independently an integer of 2 to 4, or
  at least one of $Y_1$ or $Y_2$ is not hydrogen, and when one of $Y_1$ or $Y_2$ is hydrogen, the remaining one of $Y_1$ or $Y_2$ is not an unsubstituted phenyl group or an unsubstituted methyl group.

10. The organic electroluminescence device of claim 9, wherein K1 is $1 \times 10^9$ s$^{-1}$ or less.

11. The organic electroluminescence device of claim 9, wherein the first compound further satisfies the following Equation 2:

$$Vn < 1.5 \times 10^{-4} \text{ (atomic unit)}, \quad \text{Equation 2}$$

where Vn is defined with respect to the n-th triplet excitation state and is a maximum value among off-diagonal vibronic coupling constants against each standard vibration mode calculated by quantum chemical calculation between the n-th triplet excitation state and the lowest triplet excitation state.

12. The organic electroluminescence device of claim 9, wherein a maximum emission wavelength is 480 nm or less.

13. The organic electroluminescence device of claim 9, wherein the first compound is at least one selected from compounds represented in the following Compound Group 1:

Compound Group 1
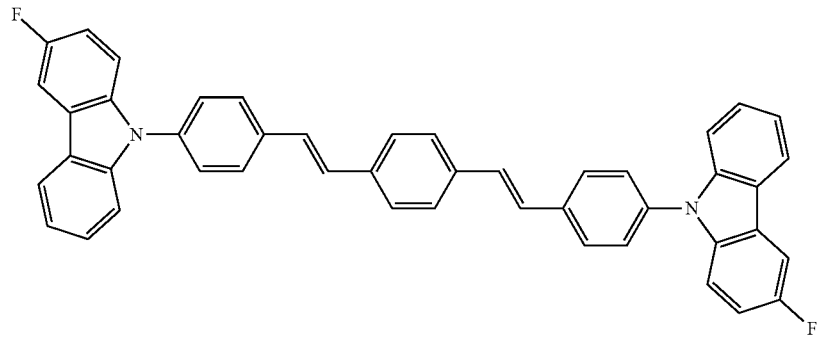
1-4
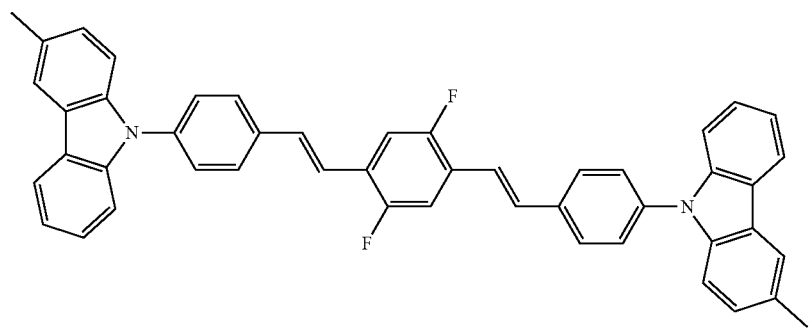
1-5
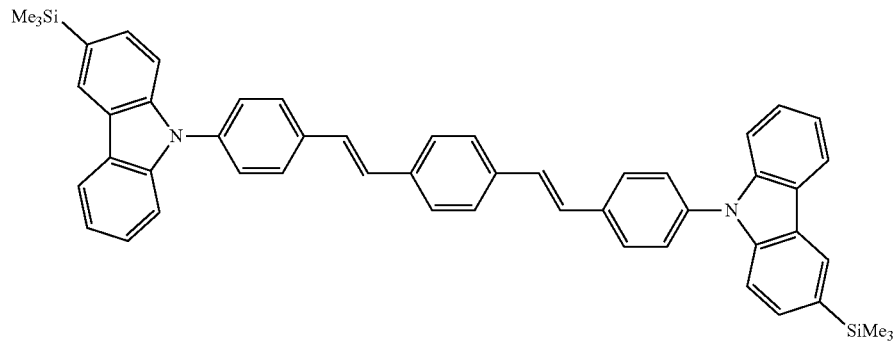
1-8
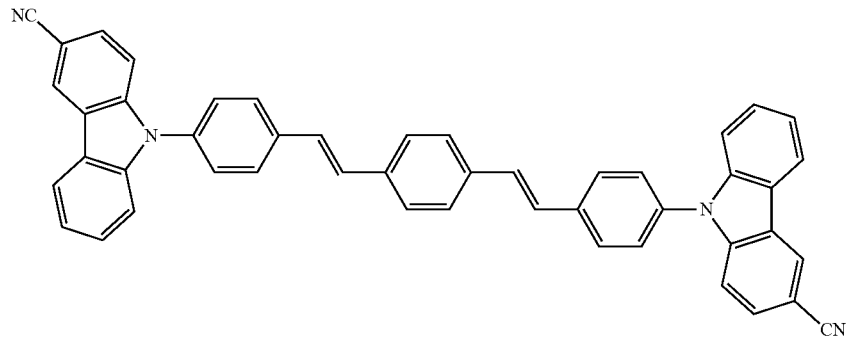
1-9

1-10
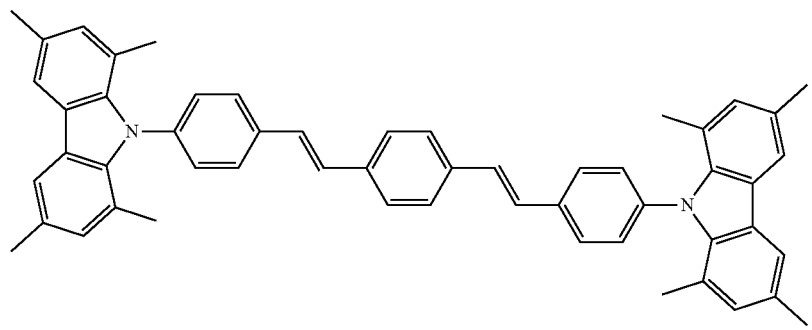
1-12
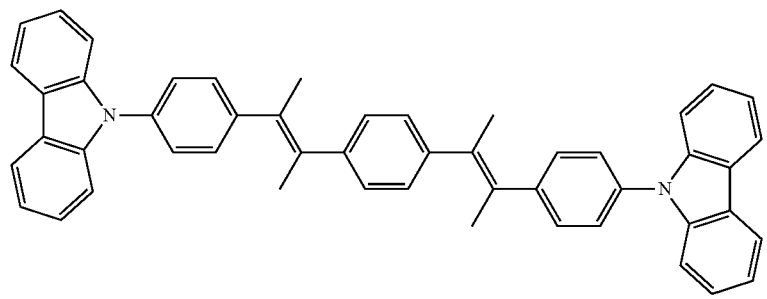
1-18
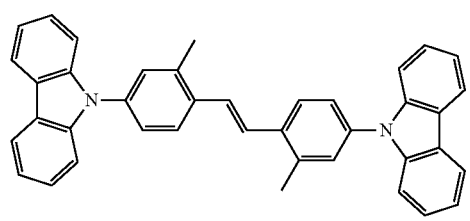
1-20
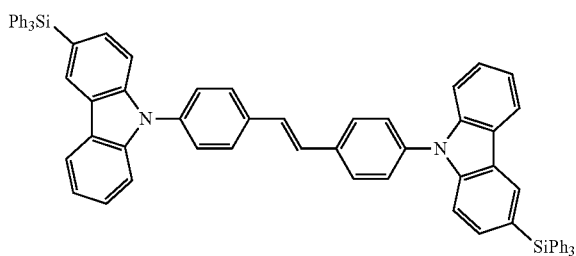
1-28
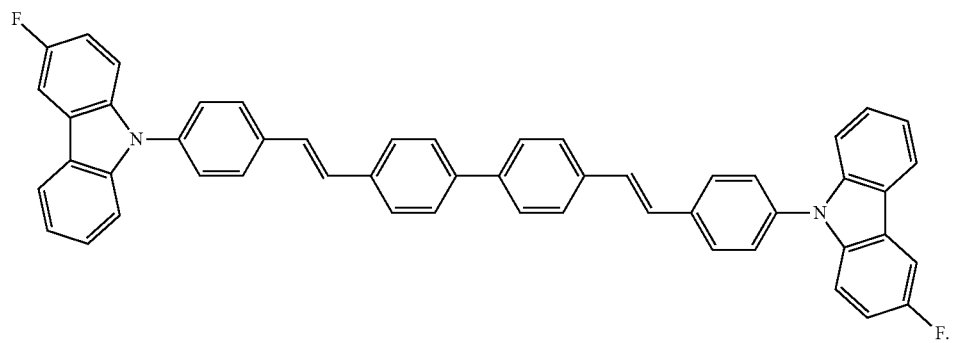

14. The organic electroluminescence device of claim 9, wherein the emission layer comprises a host and a dopant, and the dopant is the first compound.

15. The organic electroluminescence device of claim 14, wherein the lowest triplet excitation energy level of the host is higher than the lowest singlet excitation energy level of the dopant.

16. The organic electroluminescence device of claim 14, wherein the host is a second compound represented one of the following Formulae 4 to 6:

Formula 4

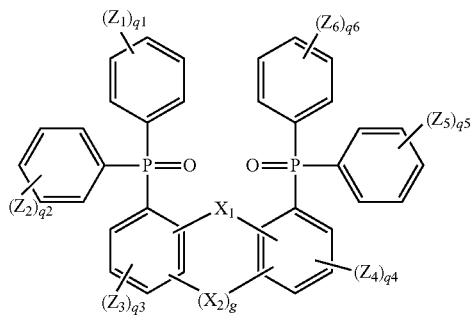

Formula 5

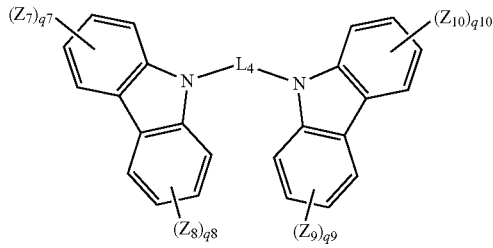

Formula 6

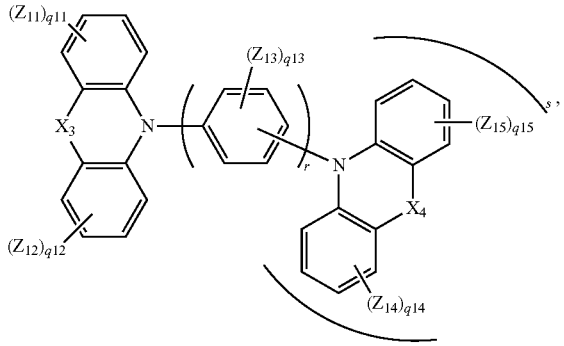

wherein $X_1$ to $X_4$ are each independently O, S, CRaRb, or SiRcRd,

Ra to Rd and $Z_1$ to $Z_{15}$ are each independently selected from hydrogen, deuterium, a halogen atom, a substituted or unsubstituted alkyl group having 1 to 20 carbon atoms, a substituted or unsubstituted aryl group having 6 to 30 carbon atoms for forming a ring, and a substituted or unsubstituted heteroaryl group having 2 to 30 carbon atoms for forming a ring, g and s are each independently 0 or 1, r is 1 or 2, $q_1$, $q_2$, $q_5$, $q_6$ and $q_{13}$ are each independently an integer of 0 to 5;

$q_3$, $q_4$, $q_7$ to $q_{12}$, $q_{14}$ and $q_{15}$ are each independently an integer of 0 to 4, and $L_4$ is a substituted or unsubstituted arylene group having 6 to 30 carbon atoms for forming a ring, or a substituted or unsubstituted heteroarylene group having 2 to 30 carbon atoms for forming a ring.

17. The organic electroluminescence device of claim 9, wherein the emission layer is a fluorescence emission layer, and a maximum external quantum yield is 5% or more.

* * * * *

UNITED STATES PATENT AND TRADEMARK OFFICE
CERTIFICATE OF CORRECTION

| | | |
|---|---|---|
| PATENT NO. | : 12,268,088 B2 | Page 1 of 2 |
| APPLICATION NO. | : 15/855898 | |
| DATED | : April 1, 2025 | |
| INVENTOR(S) | : Junta Fuchiwaki et al. | |

It is certified that error appears in the above-identified patent and that said Letters Patent is hereby corrected as shown below:

In the Claims

In Column 52, Lines 48-61, in Claim 7, Formula 6, delete

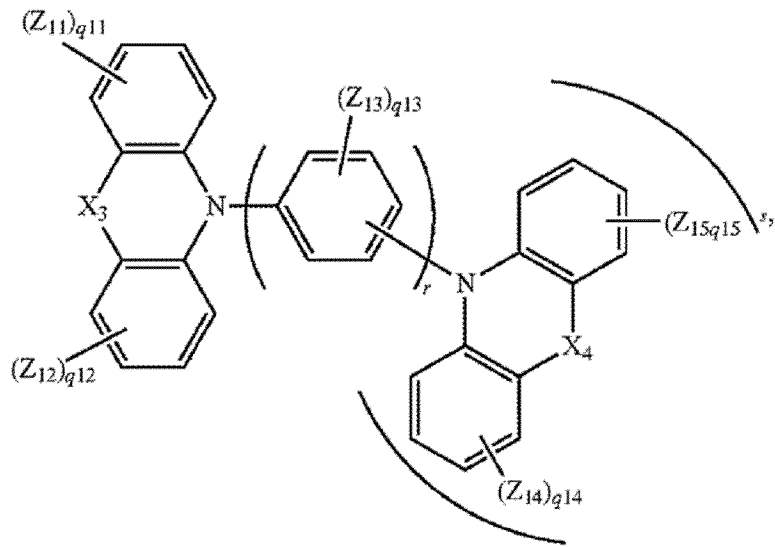

" and insert

Signed and Sealed this
Tenth Day of February, 2026

John A. Squires
*Director of the United States Patent and Trademark Office*

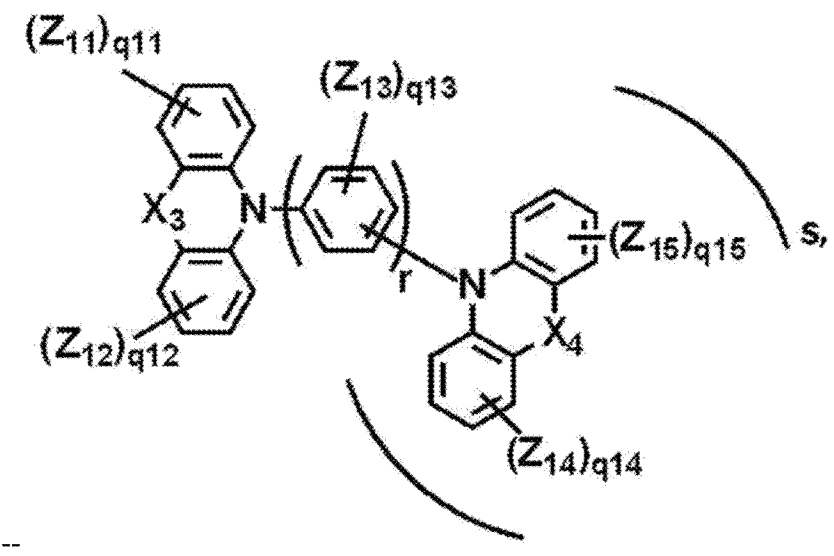
In Column 53, Line 64, in Claim 9, delete "Li" and insert -- $L_1$ --.